United States Patent
Lin et al.

(10) Patent No.: US 11,169,149 B2
(45) Date of Patent: Nov. 9, 2021

(54) PATTERNING SILICA ISLANDS ONTO THERMOPLASTIC SHRINK FILM

(71) Applicant: The Regents of the University of California, Oakland, CA (US)

(72) Inventors: Sophia Lin, Irvine, CA (US); Michelle Khine, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1020 days.

(21) Appl. No.: 14/967,145

(22) Filed: Dec. 11, 2015

(65) Prior Publication Data
US 2016/0169877 A1 Jun. 16, 2016

Related U.S. Application Data

(60) Provisional application No. 62/090,852, filed on Dec. 11, 2014.

(51) Int. Cl.
| | |
|---|---|
| *G01N 33/543* | (2006.01) |
| *B05D 3/02* | (2006.01) |
| *B05D 3/14* | (2006.01) |
| *G01N 33/552* | (2006.01) |
| *C23C 18/12* | (2006.01) |
| *C23C 18/06* | (2006.01) |
| *C23C 18/04* | (2006.01) |

(52) U.S. Cl.
CPC ......... *G01N 33/5436* (2013.01); *C23C 18/04* (2013.01); *C23C 18/06* (2013.01); *C23C 18/127* (2013.01); *C23C 18/1212* (2013.01); *C23C 18/1233* (2013.01); *C23C 18/1254* (2013.01); *G01N 33/54353* (2013.01); *G01N 33/552* (2013.01)

(58) Field of Classification Search
CPC ..... C23C 18/04; C23C 18/06; C23C 18/1212; C23C 18/1233; C23C 18/1254; C23C 18/127; G01N 33/54353; G01N 33/552; G01N 33/5436
See application file for complete search history.

(56) References Cited

U.S. PATENT DOCUMENTS

| | | | | |
|---|---|---|---|---|
| 2002/0160296 A1* | 10/2002 | Wolk | ................. | H01L 51/5293 430/200 |
| 2005/0176003 A1* | 8/2005 | Yokoyama | ....... | G01N 33/54353 435/6.11 |
| 2006/0222564 A1* | 10/2006 | Dale | ..................... | C12Q 1/001 422/400 |
| 2010/0233429 A1* | 9/2010 | Goshoo | ............ | G01N 33/54353 428/138 |
| 2015/0037802 A1* | 2/2015 | Wang | ................. | B01D 67/0088 435/6.12 |

OTHER PUBLICATIONS

Walcarius et al., "Analytical Chemistry with Silica Sol-Gels: Traditional Routes to New Materials for Chemical Analysis," Annu. Rev. Anal. Chem., 2009, vol. 2, pp. 121-143.*
Klein, "Sol-Gel Processing of Silicates,"Annu. Rev. Mater. Sci., 1985, vol. 15, No. 1, pp. 227-248.*
Lin et al., "Shrink-Induced Silica Structures for Far-field Fluorescence Enhancements,"Adv. Opt. Mater., 2013, No. 1, pp. 568-572, Published online: Jun. 21, 2013.*
Suzuki et al., "Sol-gel based fabrication of hybrid microfluidic devices composed of PDMS and thermoplastic substrates," Sensors Actuators B: Chemical, 2010, vol. 148, issue 1, pp. 323-329.*
Lewetal., "Shrink-induced single-cell plastic microwell array," J. Lab. Autom., 2011, vol. 16, No. 6, pp. 450-456.*

* cited by examiner

*Primary Examiner* — Galina M. Yakovleva
(74) *Attorney, Agent, or Firm* — Knobbe, Martens, Olson & Bear, LLP

(57) ABSTRACT

The disclosure relates to methods and devices for measuring samples, such as biological samples, especially those at low abundance, with high sensitivity and at low cost. A sample is disposed on a shrinkable scaffold and the shrinkable scaffold is shrunk, reducing the area where the sample is distributed, so as to effectively concentrate the sample on the surface of the scaffold. In the event that a biological sample is covalently attached to a scaffold having a silica structure, the increase in signal enhancement is also due to optical effects stemming from covalent linkage of the biological sample onto the silica structure of the scaffold. Silica ($SiO_2$) may be deposited onto a surface of a polymer film by functionalizing the surface of the polymer film to bind silica from a sol-gel solution, and coating the film with a sol-gel solution containing silica precursors, wherein solid silica from the sol-gel solution is deposited onto the surface of the polymer film. Also disclosed is an immunoassay platform comprising a silica-encapsulated first detection agent deposited on a polymer substrate.

5 Claims, 18 Drawing Sheets

PATTERNING SILICA ISLANDS ONTO THERMOPLASTIC SHRINK FILM

STATEMENT REGARDING FEDERALLY SPONSORED R&D

This invention was made with government support under funds awarded from the BEST IGERT program funded by the National Science Foundation DGE-1144901. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The invention disclosed herein related to the field of detection of biological samples.

Description of the Related Art

The amount of a sample available for clinical diagnostics is typically limited or the concentration is low, which makes accurate detection difficult. Therefore, there is an unmet market need for methods and devices for assaying samples with high sensitivity.

Silica is used as a platform for biofunctionalization. Deposition of the crystalline material can be expensive. Sol-gel processing, which involves producing solid materials from aqueous solutions, is a cheaper alternative used to fabricate glass or ceramic materials.

Existing methods for sol-gel depositing involve spray coating, dip-casting, and spin coating. Sol-gel deposition also includes pin-printing using a dispenser.

Spray coating, dip-casting, and spin coating result in uncontrollable regions of sol-gel material. Pin-printing of sol-gels require optimization of sol-gel composition to prevent tip clogging and pre-mature sol-gel gelation

SUMMARY OF THE INVENTION

The present disclosure provides methods and devices for measuring samples, such as biological samples, especially those at low abundance, with high sensitivity and at low cost. In one embodiment, a sample is disposed on a shrinkable scaffold, and then the shrinkable scaffold is shrunk, reducing the area where the sample is distributed, so as to effectively concentrate the sample on the surface of the scaffold. The increase of concentration can be many fold and lead to greatly increased sensitivity of detection.

It is further contemplated that, in the event that a biological sample, e.g., protein or nucleic acid, is covalently attached to a scaffold having a silica structure, the great increase in signal enhancement is also due to the optical effects stemming from covalent linkage of the biological sample onto the silica structure of the scaffold.

Thus, in one embodiment, the present disclosure provides a method for preparing a sample for detection, comprising shrinking a thermoplastic material comprising a sample disposed on the thermoplastic material, thereby concentrating the sample on the thermoplastic material.

Likewise, another embodiment provides a method for detecting a sample comprising (A) disposing the sample on a thermoplastic material, (B) shrinking the thermoplastic material, and (C) detecting the sample.

In one aspect, the sample comprises a detectable label. In another aspect, the detectable label comprises a fluorescent agent. In yet another aspect, the sample is a biological sample.

In some aspects, detecting comprises measuring the amount of a signal emitted by the sample. If the sample comprises a detectable label, detection can be done by measuring emission of the detectable label. If the sample is not labeled, a detectable label can be added so that it binds to the samples effecting detection of the sample.

The material can be pre-stressed prior to shrinking. When the material is prestressed, the shrinking can be achieved by removing the stress. In another aspect, the shrinking is achieved by heating the material, whether the material has been prestressed.

In some aspects, the shrinking is uniaxial or biaxial. In some aspects, the material is shrunk by at least 60% or more.

Thermoplastic materials suitable for practicing the present technology include, without limitation, a high molecular weight polymer, polyolefin, polyethylene, acrylonitrile butadiene styrene (ABS), acrylic, celluloid, cellulose acetate, ethylene-vinyl acetate (EVA), ethylene vinyl alcohol (EVAL), fluoroplastics (polytetrafluoroethylenes (PTFEs), including fluorinated ethylene propylene (FEP), perfluoroalkoxy alkanes (PFA), chlorotrifluoroethylene (CTFE), ethylene chlorotrifluoroethylene (ECTFE), ethylene tetrafluoroethylene (ETFE)), ionomers, KYDEX®, a trademarked acrylic/polyvinyl chloride (PVC) alloy, liquid crystal polymer (LCP), polyacetal (POM or Acetal), polyacrylates (Acrylic), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyalkanoates (PHAs), polyketone (PK), polyester polyethylene (PE), polyetheretherketone (PEEK), polyetherimide (PEI), polyethersulfone (PES), polysulfone polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC) or spectralon. In one aspect, the thermoplastic material comprises polyolefin. In another aspect, the thermoplastic material comprises polyethylene.

Also provided is a substrate having a textured surface prepared by a method of any one of above embodiments.

Sol-Gel Deposition of SiO$_2$

Some embodiments relate to a method of depositing silica (SiO2) onto a surface of a polymer film comprising: functionalizing the surface of the polymer film to bind silica from a sol-gel solution containing silica precursors; and coating the film with the sol-gel solution containing silica precursors, wherein solid silica from the sol-gel solution is deposited onto the surface of the polymer film.

Some embodiments comprise functionalizing the surface of the polymer film to comprise hydroxyl groups.

In some embodiments, the polymer film is a shrinkable thermoplastic material.

In some embodiments, the thermoplastic material comprises a high molecular weight polymer, polyolefin, a shape memory polymer, polyethylene, acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, an acrylic/PVC alloy, liquid crystal polymer (LCP), polyacetal (POM or Acetal), polyacrylates (Acrylic), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyalkanoates (PHAs), polyketone (PK), polyester polyethylene (PE), polyetheretherketone (PEEK), polyetherimide (PE1), polyethersulfone (PES), polysulfone polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC) or spectralon.

Some embodiments further comprise heat-shrinking the polymer film.

In some embodiments, the functionalizing the surface of the polymer film to comprise hydroxyl groups is achieved by plasma treatment.

In some embodiments, the plasma used in said plasma treatment is oxygen plasma.

In some embodiments, the the silica deposited onto the surface of the polymer film is selectively patterned on the polymer film.

In some embodiments, a shadow mask is used to selectively pattern the silica onto the surface of the polymer film.

In some embodiments, a biological agent is combined with the sol-gel solution, prior to deposition onto the surface of the polymer film, wherein the biological agent is encapsulated with the silica deposited on the surface of the polymer film.

Some embodiments comprise binding a biological agent to silica already deposited onto the surface of the polymer film.

Some embodiments relate to an immunoassay platform comprising a silica-encapsulated first detection agent deposited on a polymer substrate.

In some embodiments, the first detection agent is selected from the group consisting of an antibody, a protein, a polypeptide and a nucleic acid.

Some embodiments relate to a method of making a immunoassay platform comprising: functionalizing a surface of a polymer film to comprise hydroxyl groups; and coating the film with a sol-gel solution containing silca and the first detecting agent, wherein solid silica, encapsulating the first detecting agent, is deposited onto the surface of the polymer film.

Some embodiments relate to an immunoassay platform comprising a polymer substrate with silica disposed on the polymer substrate and a detection agent linked to said silica.

Some embodiments relate to an immunoassay to detect an analyte comprising: providing an immunoassay platform as described herein, wherein the first detection agent is configured to bind to the analyte; adding a sample containing the analyte to said platform; adding a second detection agent, which binds to the analyte bound to the first detection agent; and detecting a signal from the second detection agent, wherein the signal indicates the presence of said analyte in the sample.

Some immunoassays further comprise shrinking the polymer substrate prior to detecting said signal from the second detection agent.

In some embodiments, the second detection agent comprises a detectable label.

In some embodiments, the detectable label comprises a fluorescent agent.

In some embodiments, the analyte can be detected with about a 10-fold higher sensitivity compared to a control immunoassay where the first detection agent is not encapsulated by, or linked to silica deposited on the surface of the polymer film.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

DETAILED DESCRIPTION OF THE PREFERRED EMBODIMENT

Definitions

Figure 1:
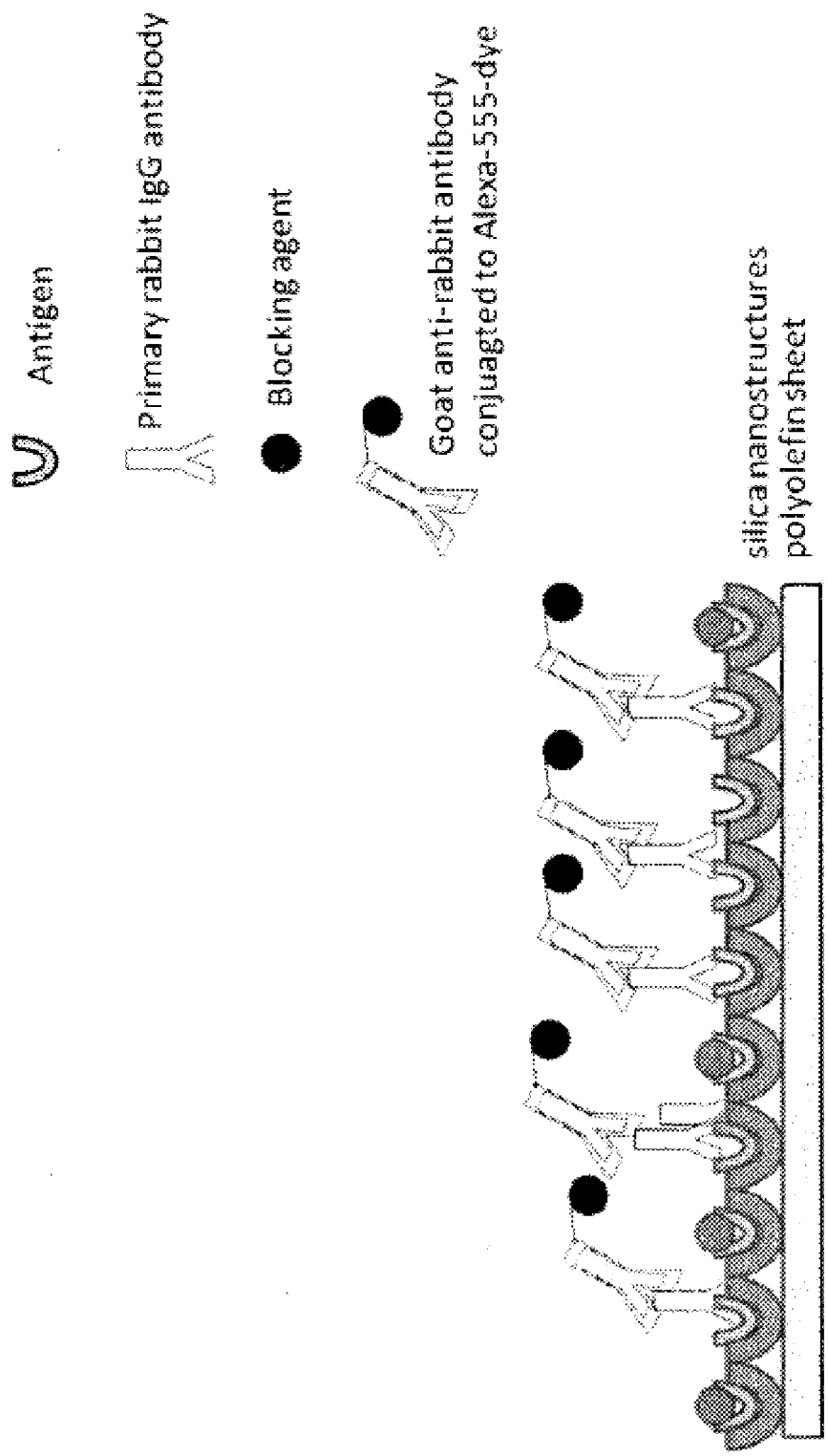
FIG. 1 is a schematic representation of the immunoassay on the silica nanostructures. Bodily fluid such as saliva is deposited on pre-shrunk silica and then incubated with the primary rabbit IgG antibody. The substrate is blocked with BSA before IgG washed with PBS. Secondary goat anti-rabbit antibody IgG conjugated with Alexa 555 dye is added and left to incubate for 1 hour before being washed again with PBS. The substrate is heat shrunk in an oven before imaged using a fluorescence microscope.
Figure 2:
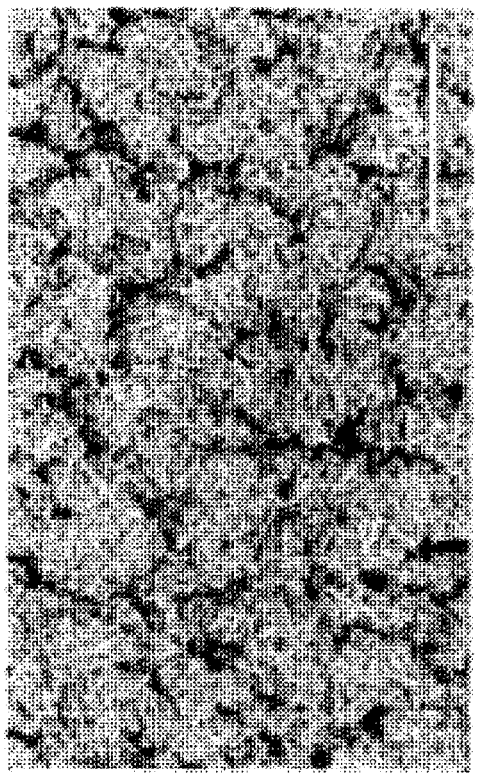
FIG. 2. (A), (B), (C) and (D) show microscopic pictures of a textured surface of the film at indicated magnification levels.
Figure 2:
Figure 2:
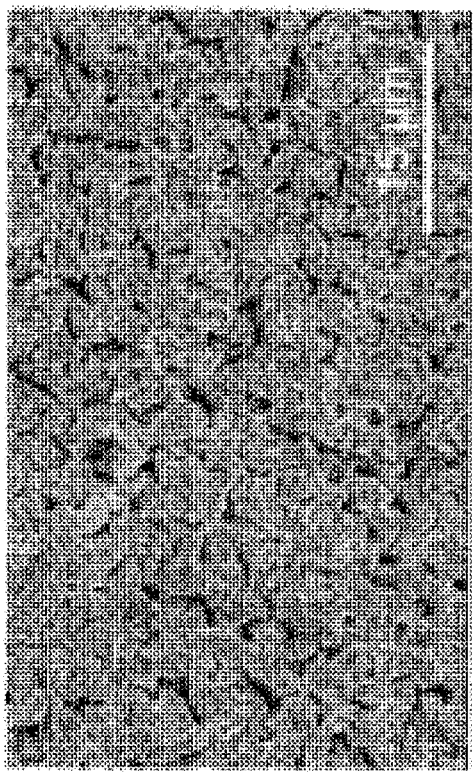
Figure 2:

As used herein, certain terms may have the following defined meanings

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps for preparing the intended device. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

A "thermoplastic material" is intended to mean a plastic material which shrinks upon heating or upon release of prestress such as a stress created by stretching. In one aspect, the thermoplastic materials are those which shrink uniformly without distortion. The shrinking can be either bi-axially (isotropic) or uni-axial (anisotropic). Suitable thermoplastic materials for inclusion in the methods of this invention include, for example, shape memory polymers, polyolefin, polyethylene, high molecular weight polymers such as acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, a trademarked acrylic/PVC alloy, liquid crystal polymer (LCP), polyacetal (POM or Acetal), polyacrylates (Acrylic), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyalkanoates (PHAs), polyketone (PK), polyester polyethylene (PE), polyetheretherketone (PEEK), polyetherimide (PEI), polyethersulfone (PES), polysulfone polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC) and spectralon.

In some aspects, the thermoplastic material encompasses polyolefin. A polyolefin is a polymer produced from a simple olefin (also called an alkene) as a monomer. For example, polyethylene is the polyolefin produced by polymerizing the olefin ethylene. Polypropylene is another common polyolefin which is made from the olefin propylene.

In some aspects, the thermoplastic material encompasses shape memory polymers (SMPs). SMPs are polymeric smart materials that have the ability to return from a deformed state (temporary shape) to their original (permanent) shape induced by an external stimulus (trigger), such as temperature change.

Commercially available thermoplastic materials include, without limitation, "Shrinky-Dink" and Solupore®. Shrinky-Dink is a commercial thermoplastic which is used a children's toy. Solupore® is available from Lydall, Inc. of Manchester, Conn.

As used herein, "labels" or "detectable labels" are chemical or biochemical moieties useful for labeling a nucleic acid. "Labels" include fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to an oligonucleotide or nucleotide.

In illustrative embodiments, the antibodies may be labeled with a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes and/or dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (B is aminophenylox adiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3. 1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP(S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant lavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613[PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™;

Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

Methods for Preparing a Sample for Analysis

One embodiment of the present disclosure provides a method for preparing a sample for detection, comprising shrinking a thermoplastic material comprising a sample disposed on the thermoplastic material, thereby concentrating the sample on the thermoplastic material.

Likewise, another embodiment provides a method for detecting a sample comprising: (A) disposing the sample on a thermoplastic material, (B) shrinking the thermoplastic material, and (C) detecting the sample.

In one aspect, the sample comprises a detectable label. In another aspect, the detectable label comprises a fluorescent agent. In yet another aspect, the sample is a biological sample.

The thermoplastic material can be pre-stressed prior to shrinking. In such a case, the shrinking can be achieved by removing the stress. Such a stress can simply be stretching, either uniaxially or biaxially.

Alternatively, the shrinking can be achieved by heating the material. Depending on the material and desired scale of texture, the temperature can vary. In one aspect, the heating is at least about 200° F., or at least about 250° F., or at least about 275° F., or at least about 300° F., or at least about 350° F.

In some aspects, the material is treated with a plasma before the shrinking. It has been demonstrated that plasma treatment of a thermoplastic material, such as a polyethylene (PE) film, creates a stiff layer at the surface of a relatively softer bulk PE. Leveraging the inherent refraction properties of the thermoplastic material at elevated temperature, the mismatch in stiffness between two layers will cause the stiff outer layer to buckle and form controllable textures or wrinkles.

Plasmas can be prepared with methods known in the art and can vary depending on availability of sources. In one embodiment, the plasma is oxygen plasma, helium plasma, or hydrogen plasma. In a particular embodiment, the plasma is oxygen plasma.

The duration of plasma treatment can vary and depend on the desired scale of the texture and/or the thermoplastic material, for instance. In one aspect, the plasma treatment takes more than about 10 seconds, or alternatively more than about 20 seconds, about 30 seconds, about 1 minute, about 2 minutes, about 3 minutes, about 4 minutes, about 5 minutes, about 7 minutes, about 10 minutes, about 15 minutes, about 20 minutes, about 25 minutes, or about 30 minutes. In another aspect, the plasma treatment takes less than about 60 minutes, or alternatively less than about 45 minutes, about 30 minutes, about 25 minutes, about 20 minutes, about 15 minutes, about 10 minutes, about 7 minutes, about 5 minutes, about 4 minutes, about 3 minutes, about 2 minutes, about 1 minute, about 30 seconds, or about 20 seconds. In some aspects, the treatment is carried out in a closed chamber. In some aspects, the treatment is carried out in a handheld corona discharger.

The thermoplastic material can be pre-stressed prior to the plasma treatment. In such a case, the shrinking can be achieved by removing the stress. Such a stress can simply be stretching, either uniaxially or biaxially.

Alternatively, the shrinking can be achieved by heating the material. Depending on the material and desired scale of texture, the temperature can vary. In one aspect, the heating is at least about 200° F., or at least about 250° F., or at least about 275° F., or at least about 300° F., or at least about 350° F.

Shrinking of the material can be uniaxial or biaxial. When the material is shrunk uniaxially, the texture may be one dimensional. When the material is shrunk biaxially, the texture may be two dimensional.

In some embodiments, the material is shrunk, uniaxially or biaxially, by at least about 60%, or alternatively at least about 70%, about 75%, about 80%, about 85%, about 90%, about 91%, about 92%, about 93%, about 94%, about 95%, about 96%, about 97%, about 98%, or about 99% from its original size.

Still, in some aspects, the material is etched, prior to deposition of the sample, to provide room for holding the sample. Such etching, in one embodiment, also contributes to the enhanced signal detection. Methods of etching and related shrinking are provided in WO 2009/064816, the content of which is incorporated into the present disclosure in its entirety, by reference.

In one aspect, the sample is attached to the material. The attachment can be covalent or non-covalent. In one aspect, the attaching is covalent. In a particular aspect, the covalent attachment involves a linker, such as but not limited to, biotin and Poly (L-glutamic acid) (Pglu). In one aspect, the sample is a biological sample, including but not limited to protein, nucleic acids, such as DNA and RNA.

Shrinking of the material can be uniaxial or biaxial. When the material is shrunk uniaxially, the texture may be one dimensional. When the material is shrunk biaxially, the texture may be two dimensional.

In some embodiments, the material is shrunk, uniaxially or biaxially, by at least about 60%, or alternatively at least about 70%, about 75%, about 80%, about 85%, about 90%, about 91%, about 92%, about 93%, about 94%, about 95%, about 96%, about 97%, about 98%, or about 99% from its original size.

In some embodiments, the concentration of the sample is increased by at least about 5 fold, or alternatively about 5, or about 6, or about 7, or about 8, or about 9, or about 10, or about 12, or about 14, or about 16, or about 18, or about 20, or about 25, or about 30, or about 40, or about 50, or about 60, or about 70, or about 80, or about 90, or about 100 or about 200 fold.

Further, some embodiments of the present disclosure provide samples prepared by any of the disclosed methods.

Selective Patterning of $SiO_2$

Some embodiments are directed to a method to selectively pattern liquid silica, with or without the inclusion of biological specimens, onto surfaces and to inventive apparatuses that can be produced in such methods. This is useful because it allows for discrete regions where biological agents can be deposited. Fabricated surfaces can then be further used for specimen concentration and detection.

In certain embodiments, a method is provided to selectively pattern silica onto treated surfaces. The techniques described allow for customizable regions of sol-gel deposition by simply changing the design of the shadow mask. This process does not require complicated machining. It is less expensive, more customizable, and the time constraint is limited by the time it takes to prepare the shadow mask, which can be done using common computer design software.

Figure 15:
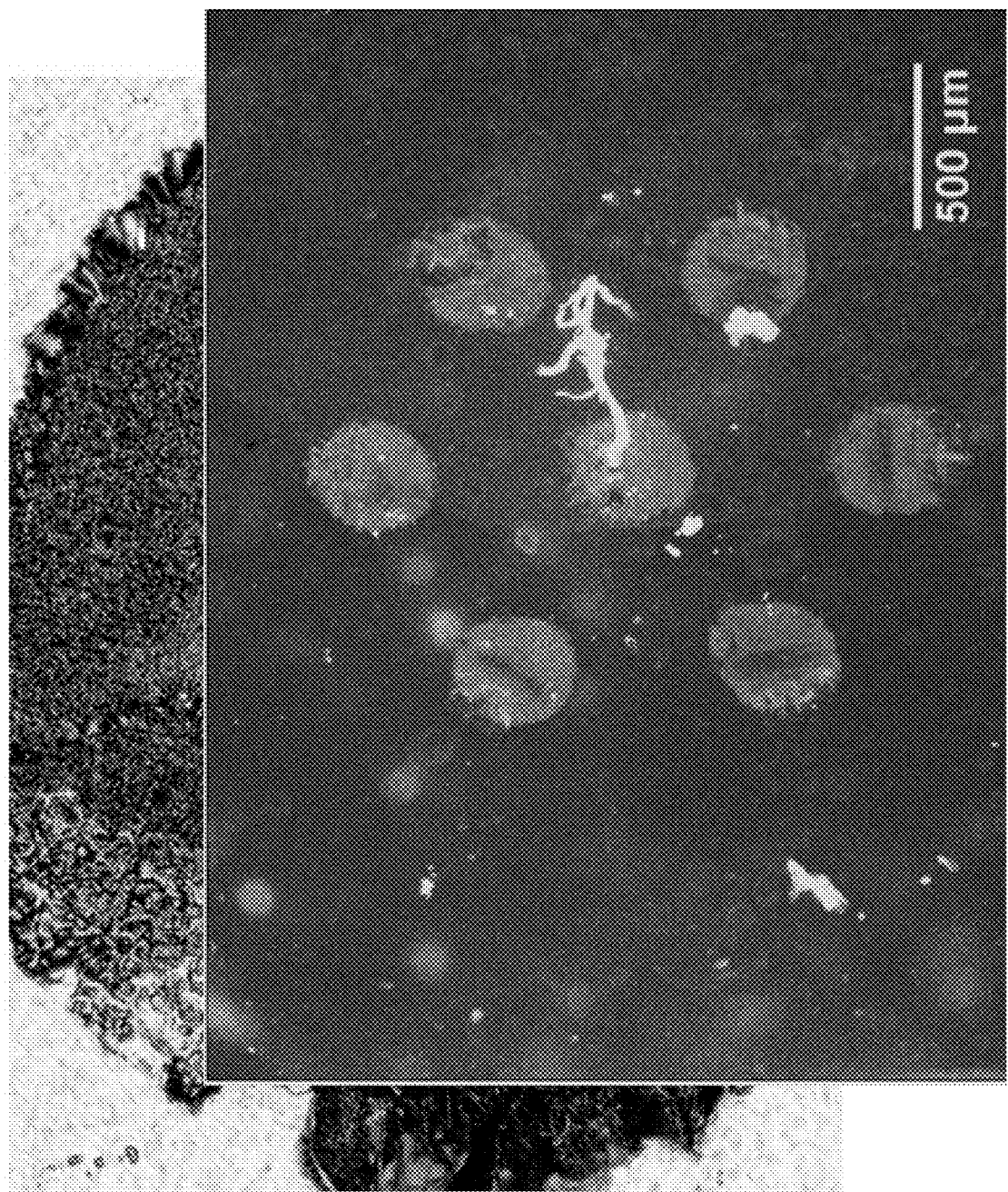
FIG. 15. Patterning of discrete regions: circular regions of silica are shown.

We have demonstrated the ability to pattern discrete regions. FIG. 15 shows a circular region of silica. Enhanced embodiments include the use of the silica islands as an immobilization platform for biological agents.

Surface Structures Enhance Fluorescence Signal Detection

Examples of effective surface structures for fluorescence signal enhancement include metal nanostructures and nanoparticles that couple excitation with surface plasmons and photonic crystals that act as optical resonators. Enhancement of fluorescent properties can be achieved through covalent encapsulation of dye into $SiO_2$-based nanoparticles. Studies of dye-encapsulated $SiO_2$ nanoparticles have suggested that these photophysical changes are dependent on internal architecture of the $SiO_2$ structures. Immobilization of the fluorescent dye within the $SiO_2$ core-shell is suggested to restrict molecular mobility, which can lead to reduced nonradiative relaxation and subsequently increased quantum yield. $SiO_2$ encapsulation has also been reported to result in enhancement of radiative decay rate due to the difference between the refractive indices of rhodamine dyes and $SiO_2$ surroundings. Leveraging these properties, as well as the mechanical stability and chemical versatility of $SiO_2$, we develop a strategy to create a robust and scalable fluorescence enhancing platform based on low-cost commodity shrink wrap film.

Dense multiscale silica ($SiO_2$) micro- and nanostructures are fabricated on a polymer film. In some embodiments, the $SiO_2$ substrate serves as a robust platform to enhance the fluorescence signal of bound biomolecules. Through a combination of surface concentration, light scattering, and changes in the photophysical properties of confined dye molecules, dramatic fluorescence signal enhancements and an increased signal-to-noise ratio is demonstrated on $SiO_2$ structures. By covalently linking biomolecules onto a shrinkable $SiO_2$ substrate: (1) the fluorophores are brought closer in proximity to each other which results in signal concentration, (2) the $SiO_2$ structures create a highly porous surface that results in light scattering, and (3) the covalent attachment of fluorophore within the $SiO_2$ structures causes changes in the photophysical properties of the dye.

In some embodiments, the presence of silica nanostructures can result in a fluorescence signal enhancement of about 2-fold, 5-fold, 10-fold, 20-fold, 30-fold, 40-fold, 50-fold, 100-fold, 150-fold, 200-fold, 250-fold, 300-fold, 350-fold, 400-fold, 450-fold, 500-fold, or 1000-fold.

In some embodiments, low concentrations of a biological agent can be detected, for example at concentrations of 0.01 pg/mL, 0.05 pg/mL, 0.1 pg/mL, 0.5 pg/mL, 1 pg/mL, 5 pg/mL, 10 pg/mL 15 pg/mL, 20 pg/mL, 25 pg/mL, 30 pg/mL, 35 pg/mL, 40 pg/mL, 45 pg/mL, 50 pg/mL, 55 pg/mL, 60 pg/mL, 65 pg/mL, 70 pg/mL, 80 pg/mL, 85 pg/mL, 90 pg/mL, 95 pg/mL, 100 pg/mL, 110 pg/mL, 120 pg/mL, 130 pg/mL, 140 pg/mL, 150 pg/mL, 160 pg/mL, 170 pg/mL, 180 pg/mL, 190 pg/mL, 200 pg/mL, 300 pg/mL, 400 pg/mL, or about 500 pg/mL.

In some embodiments, low concentrations of a biological agent can be detected, for example at concentrations of about 1-5 pg/mL.

Sol-Gel Processing

The name sol-gel derives from the fact that micro particles or molecules in a solution (sols) agglomerate and under controlled conditions eventually link together to form a coherent network (gel).

There are two generic variations of the sol-gel technique. One is called the colloidal method, the other is called the polymeric (or alkoxide) method. The differences between the two stem from the types of starting materials (precursors) that are used.

Both methods involve suspending or dissolving the precursor(s) in a suitable liquid, usually water for the colloidal route and alcohol for the polymeric method. The precursor is then activated by the addition of an acid (such as hydrochloric acid) or a base (such as potassium hydroxide). The activated precursors then react together to form a network. The network grows and ages with time and temperature until it is the size of the container. At this point the viscosity of the liquid increases at an exponential rate until gelation occurs, that is, no more flow is observed.

Sol-gels can be processed before gelation by a range of methods including spraying to produce coatings and powders, drawing from a liquid to produce fibers and processing in a vessel to produce aerogels and monoliths.

Using sol-gel methods, protective coatings can be made at modest (e.g., less than 150° C.) temperatures. These coatings can be tailored for specific applications including: mechanical protection for soft substrates (such as plastics and metals), chemical protection for reactive substrates, and environmental protection for exposed surfaces.

Silicas can go into solution as monosilicic acids. An equation between each form of solid silica and aqueous solutions saturated with the monosilicic acid may be represented by:

$$SiO_2(s)+nH_2O=Si(OH)_4(aq)$$

In a sol-gel procedure, silica can attach to hydroxyl groups on a substrate surface.

Functionalized Surface of a Polymer Film

Polymer films can be functionalized by introducing hydroxyl groups. In some embodiments, introduction of surface hydroxyl groups is achieved by plasma treatment. In some embodiments, the plasma used is oxygen plasma.

The methods disclosed herein provide a basis for enhanced detection of labelled proteins in immunoassays. For example, the methods demonstrate specificity and selectivity via sandwich immunoassays and provide a way to lower the limit of detection (LOD) of a biological agent.

Example 1

Preparation of an Antibody for Fluoroimmunoassay.

A thin layer of silica is deposited on a heat shrink film, polyolefin, by an E-beam evaporation process. Biological molecules, in this case rabbit immunoglobin (IgG) is microcontact printed on the solid substrate and then blocked with blocking solution for 2 hours at room temperature. After 2 hours, the blocking solution is washed and then the goat anti-rabbit conjugated to AlexaFluor 555 is added and after 2 hr incubation the fluorescence signal is measured. After measuring the fluorescence signal, the sample is shrunk in an oven by heating sequentially to 115° C. for 30 minutes, 135° C. for 10 minutes, and 155° C. The inherent ability of the polyolefin polymer to shrink helps with increasing the concentration of the protein and increasing the fluorescent signal enhancement by 16 fold. The experimental procedure is illustrated in FIG. 1. FIG. 2 (A-D) show the nanostructure of the shrunk surface of the film.

Bodily fluids such as saliva which have antigens that can be recognized by the primary antibody can also be assayed the same way.

Example 2

Amplification in Sample Signal Achieved by Shrinking a Thermoplastic Surface

This example demonstrates that amplification in sample signal can be achieved by shrinking the thermoplastic surface. The amplification utilizes a protein's ability to naturally adsorb onto a surface and the subsequent increase in detection signal is attributed to concentrating the sample on the thermoplastic material and increasing the surface area. Further, the method illustrated here involves chemically functionalizing the thermoplastic material for covalent attachment of biological samples.

Modification of the clean thermoplastic surface starts with depositing a thin layer of silica onto the surface by ion beam sputter coater, followed by oxygen plasma treatment for the introduction of hydroxyl groups. The surface is then aminated by submerging into a 5% (v/v) (3-aminopropyl) trimethoxysilane (APTMS) ethanolic solution for 2 hours at room temperature. The thermoplastic substrate is then washed with 100% ethanol and ddH2O, and allowed to cure overnight at room temperature. The aminated thermoplastic surface is reacted with NHS-ester activated biotin (1 mg/ml) for 2 hrs, washed twice with 1× PBS and ddh2O, and then incubated with 1 µL volumes of streptavidin-TRITC for 2 hrs (10 µg/ml). Fluorescent signal is measured. The thermoplastic substrates are shrunk by heating to T=160° C. and fluorescent signal is measured again. This procedure is illustrated in FIG. 3a.

Figure 3:
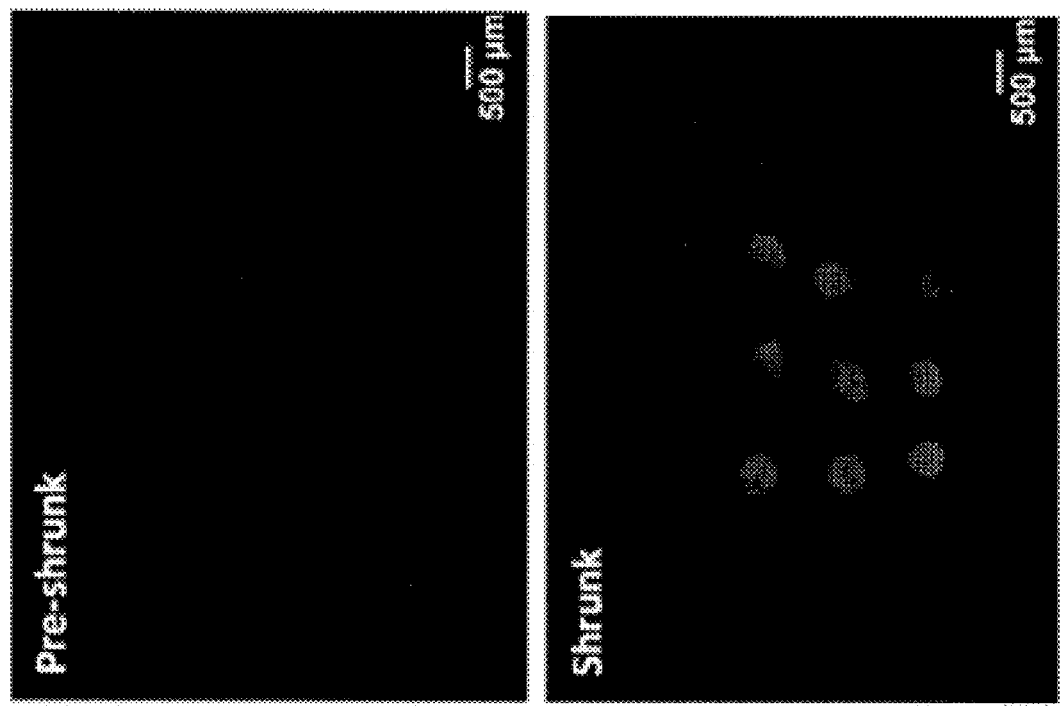
FIG. 3. (A) illustrates the process of shrinking a surface carrying a biological sample. (B) Images showing the detected signal before (upper) and after (lower) shrinking.
Figure 3:
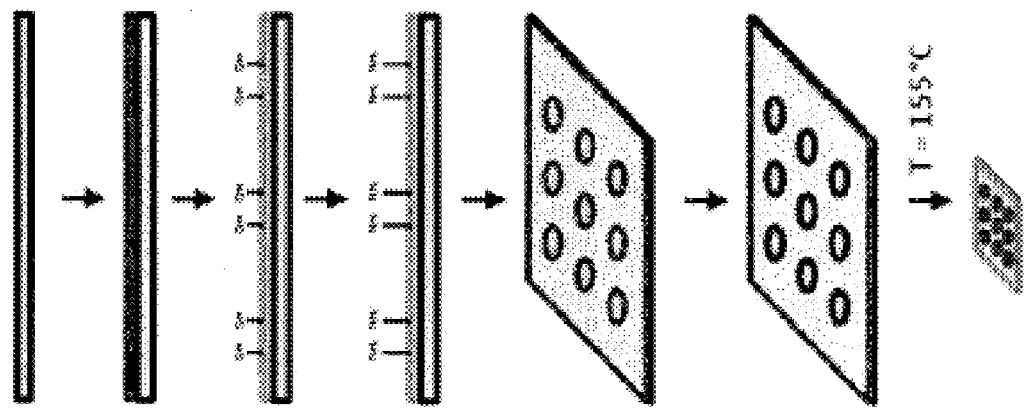
Figure 4:
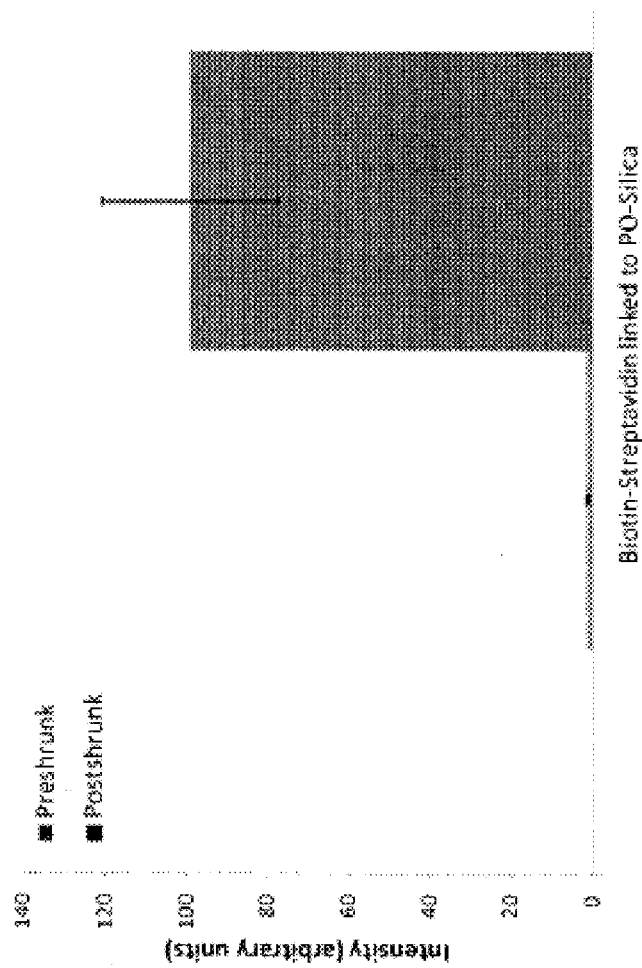
FIG. 4. A bar chart showing the detection efficiency before (left) and after (right) shrinking.

The observed fluorescent signal of the shrunk thermoplastic substrates demonstrates signal enhancement ranging between 55 to 75 fold (see actual images in FIG. 3b and comparison charts in FIG. 4).

Example 3

Amplification in Sample Signal Can be Achieved by Shrinking the Thermoplastic Surface.

This procedure involves fabricating a DNA microarray by laser etching a microwell pattern in polyolefin (PO) sealing tape and adhering to a polystyrene (PS) or PO thermoplastic. Features are etched into the exposed thermoplastic surface and silica is sputtered on top. Isopropyl alcohol (IPA) is used to remove the PO sealing tape without disturbing the silica. The exposed silica-coated wells are treated with oxygen plasma to introduce hydroxyl groups and then chemically modified with 5% (v/v) (3-aminopropyl)trimethoxysilane (APTMS) ethanolic solution for 4 hours at room temperature. Poly (L-glutamic acid) (Pglu) is then reacted with the aminated thermoplastic surface in the presence of 1-Ethyl-3-(3-dimethylaminopropyl)carbodiimide (EDC)/N-Hydroxysuccinimide (NHS). Single stranded DNA is flowed over the substrate to bind to the Pglu through the formation of amide bonds. The thermoplastic substrate is shrunk by heating to T=160° C. Complementary stranded DNA tagged with Cy3 is flowed over the shrunk substrate and fluorescent signal is measured (FIG. 5).

Figure 5:
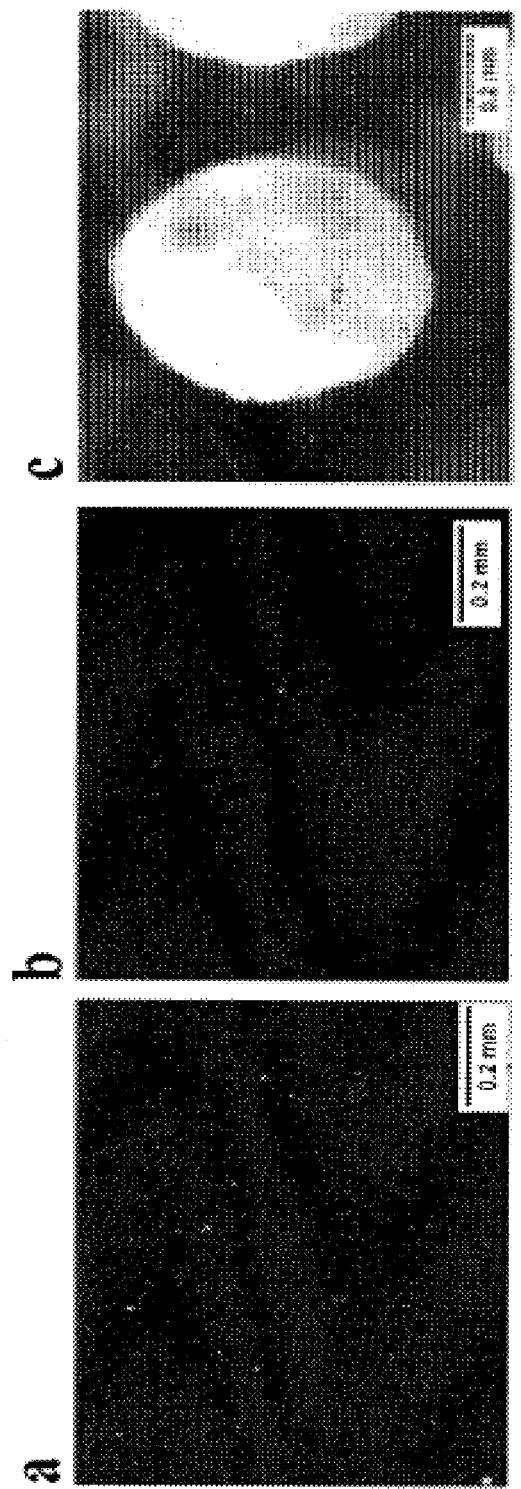
FIG. 5. Images showing the fluorescence intensity for (a) DNA hybridized on glass slide, (b) single-stranded DNA (non-hybridized) on silica polyolefin (PO), and (c) DNA hybridized on silica PO.
Figure 6:
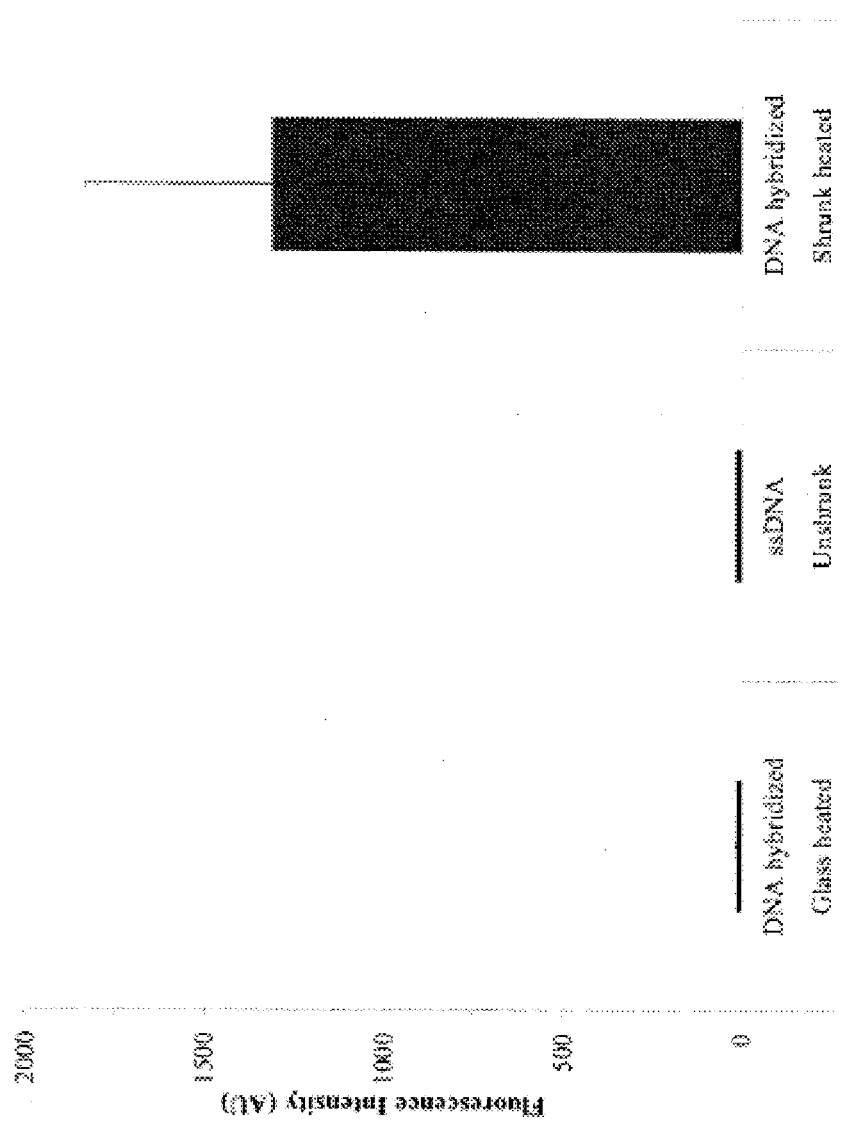
FIG. 6. A bar chart showing the detection efficiency before (left) and after (right) shrinking as reflected in the images of FIG. 5.
Figure 7:
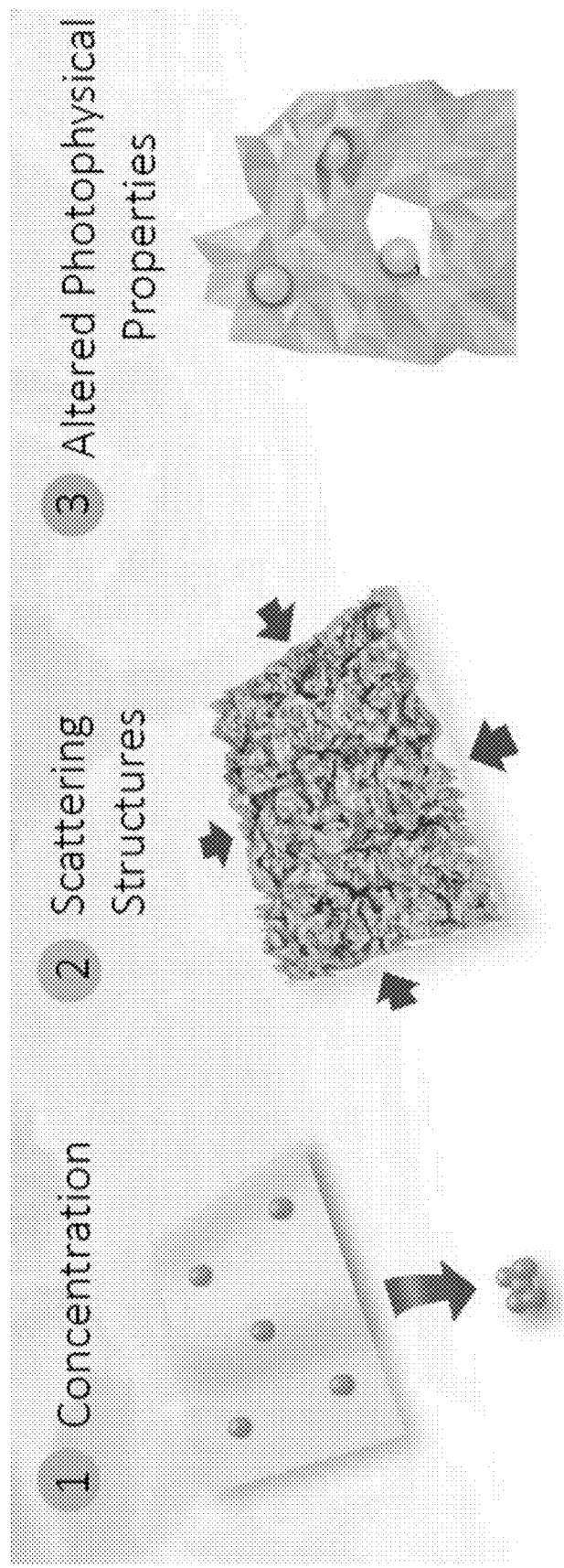
FIG. 7 illustrates some of the physical phenomena leveraged for providing fluorescence signal enhancement, including concentration, scattering structures and altered photophysical properties.

The observed fluorescent signal of biological sample shows a signal enhancement of around 90 fold (FIGS. 5 and 6).

Example 4

Shrink-Induced Silica Structures for Far-Field Fluorescence Enhancements.

Dense multiscale silica ($SiO_2$) micro- and nanostructures are fabricated on a pre-stressed polymer film (Lin et al. 2013 *Adv Optical Mater* 1: 568-572). This novel $SiO_2$ substrate serves as a robust platform to enhance the fluorescence signal of bound biomolecules. Through a combination of surface concentration, light scattering, and changes in the photophysical properties of the confined dye molecules, dramatic fluorescence signal enhancements (average=116 times greater than on planar glass) and increased signal-to-noise ratio (76:1) are demonstrated with tetramethylrhodamine isothiocyanate (TRITC)-conjugated streptavidin (STRITC) on $SiO_2$ structures. Enhanced detection sensitivity of STRITC over glass on the $SiO_2$ structures is achieved down to a detection limit of 11 ng $mL^{-1}$. Such significant fluorescence signal enhancements have importance in practical applications such disease diagnostics and surface sensing.

Introduction

Fluorescence is widely used for chemical sensing, biomolecule detection, disease diagnostics, and various applications in biology. Ongoing challenges persist in improving detection sensitivity and the signal-to-noise ratio (SNR) of low-abundance target molecules. Efforts to improve detection sensitivity and robustness of fluorescent assays have resulted in the development of brighter and more photostable fluorescent labels, (N. P. Voloshina et al. 1997 *Mol. Biol. Cell* 8: 2017-2017; and R. B. Altman et al. 2012 Nat. Methods 9: 68-U178) advancements of traditional imaging devices and techniques, (H. R. Petty et al. 2007 *Microsc. Res. Techniq.* 70: 687-709) and engineered surface structures for signal enhancement (E. D. Diebold et al. 2009 Langmuir 25: 1790-1794; P. P. Pompa et al. 2006 Nat. Nanotechnol. 1: 126-130; and A. Pokhriyal et al. 2010 *Opt. Express* 18: 24793-24808).

Examples of effective surface structures for fluorescence signal enhancement include metal nanostructures and nanoparticles that couple excitation with surface plasmons and photonic crystals that act as optical resonators (M. R. Gartia et al. 2012 *Appl. Phys. Lett.* 101; Y. Fu et al. 2007 *J. Fluoresc.* 17: 811; and W. Zhang et al. 2008 *Small* 4: 2199-2203). These structures typically use expensive materials such as gold and silver, require extensive fabrication steps for precise control of homogeneous or periodic surface features, and necessitate specialized equipment (e.g. 2-photon microscopy). Importantly, while large fluorescence enhancements have been observed, such plasmon-coupled effects suffer from practical limitations including: localized near-field effects with enhancements occurring only within nanometric lengths from the surface, heterogeneous enhancements with small areas of 'hot spots', and enhancements which are wavelength dependent. Such practical drawbacks impede progress in translating these large enhancements into solutions for deployable robust detection.

It has recently been observed that enhancements of fluorescent properties can be achieved through covalent encapsulation of dye into $SiO_2$-based nanoparticles (C. Graf et al. 1999 *Langmuir* 15: 6170-6180; J. W. Gilliland et al. 2005 *Chem. Mater.* 17: 6702-6712; M. Casalboni et al. 1997 *Appl. Phys. Lett.* 70: 2969-2971; and E. Herz et al. 2009 *J. Mater. Chem.* 19: 6341-6347). Studies of dye-encapsulated $SiO_2$ nanoparticles have suggested that these photophysical changes are dependent on internal architecture of the $SiO_2$ structures (H. Ow et al. 2005 *Nano Lett.* 5: 113-117).

Immobilization of the fluorescent dye within the $SiO_2$ core-shell is suggested to restrict molecular mobility, which can lead to reduced nonradiative relaxation and subsequently increased quantum yield (D. R. Larson et al. 2008 *Chem. Mater.* 20: 2677-2684; and D. L. Ma et al. 2009 *J. Phys. Chem. C* 113: 15974-15981). $SiO_2$ encapsulation has also been reported to result in enhancement of radiative decay rate due to the difference between the refractive indices of rhodamine dyes and $SiO_2$ surroundings (D. R. Larson et al. 2008 Chem. Mater. 20: 2677-2684; D. L. Ma et al. 2009 J. Phys. Chem. C 113: 15974-15981 and D. Toptygin et al. 2002 *J. Phys. Chem. B* 106: 3724-3734).

Leveraging these properties, as well as the mechanical stability and chemical versatility of $SiO_2$, we develop a strategy to create a robust and scalable fluorescence enhancing platform based on low-cost commodity shrink wrap film. We have previously shown that we are able to achieve concentration of adsorbed molecules by leveraging the heat-induced retraction properties of polyolefin (PO) sheets (D. Nguyen et al. 2010 *Lab Chip* 10: 1623-1626). We have also shown that the deposition of a stiff, non-shrinkable material such as metal onto the PO film results in buckling when the substrate is heated (C. C. Fu et al. 2009 *Adv. Mater.* 21; 4472). Here, we demonstrate that this strategy is extensible for $SiO_2$. We use the biotin-streptavidin hybridization as it is a versatile binding system that has been shown to form the basis of many detection methods, including DNA, protein, and aptamer sensing (T. C. Lu et al. 2008 *Acta Biomater.* 4: 1770-1777; G. Demirel et al. 2007 Surf. Sci. 601: 4563-4570; B. L. Zhang et al. 2011 *J. Biomed. Opt.* 16; H. Bal et al. 2012 *Sensors* 12: 12506-12518 and E. P. Diamandis and T. K. Christopoulos 1991 *Clin. Chem.* 137: 625-636). By covalently linking the biomolecules onto the shrinkable $SiO_2$ substrate: (1) the fluorophores are brought closer in proximity to each other which results in signal concentration, (2) the $SiO_2$ structures create a highly porous surface that results in light scattering, and (3) the covalent attachment of fluorophore within the $SiO_2$ structures causes changes in the photophysical properties of the dye. Together, this results in both dramatic increases in the signal intensity and fluorescence enhancement factor. To understand the mechanisms of such enhancements, we characterize our $SiO_2$ structures, demonstrate fluorescence signal enhancements, investigate the effects of dye-silica interaction on absorption, emission, and look into the detection sensitivity of the substrate.

Preparation of PO-$SiO_2$ Substrate and Biomolecule Attachment

Figure 16:
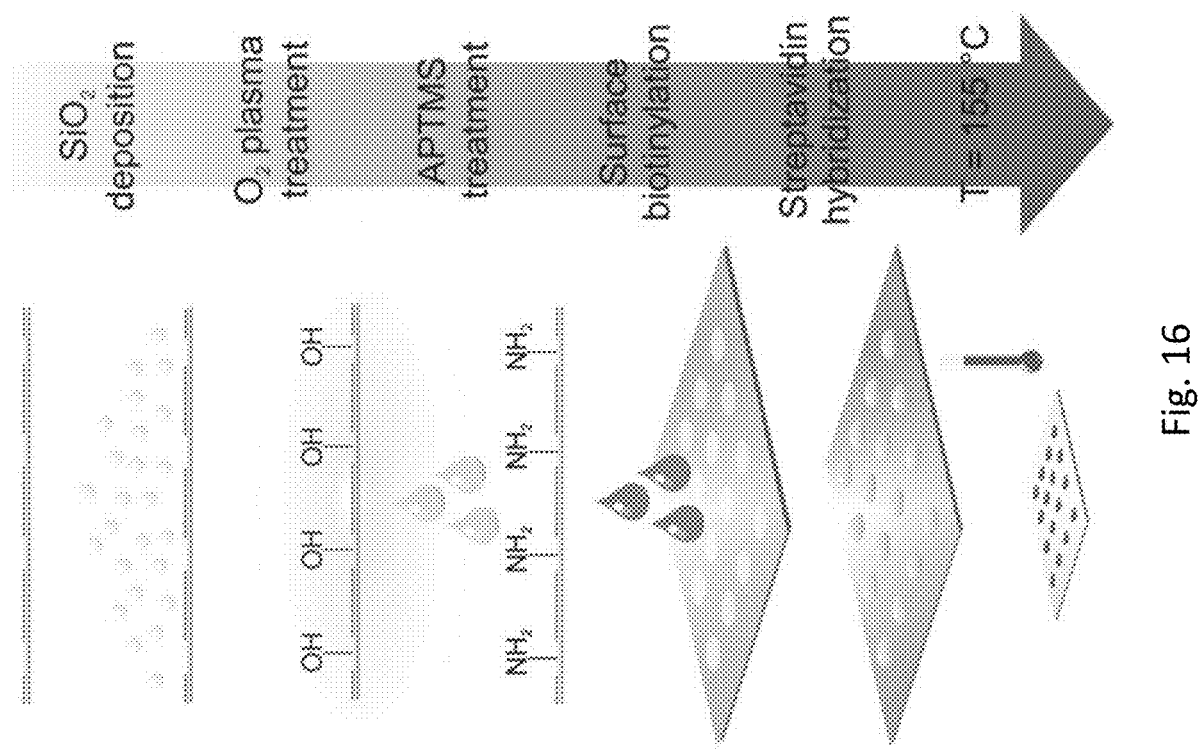
FIG. 16. Schematic illustrating the fabrication of a fluorescence enhancing PO-SiO$_2$ substrate. Clean PO is coated with a thin layer of SiO$_2$ through ion-beam sputter deposition, treated with O$_2$ plasma, and reacted with APTMS for the formation of reactive primary amines. The silanized surface was linked with biotin, reacted with STRITC, and shrunk.

We leverage the stiffness mismatch between the thin $SiO_2$ layer and the PO film to create $SiO_2$ micro- and nanostructures. The multi-scale substrate that results in enhanced fluorescence signal is prepared following the procedure illustrated in FIG. 16. Briefly, a home-made shadow mask was applied to a clean PO surface prior to sputter deposition of $SiO_2$ to form PO-$SiO_2$ substrates. The surfaces were chemically activated through $O_2$ plasma treatment and then functionalized with primary amine groups for further biomolecule attachment. The PO-$SiO_2$ surfaces were biotinylated and then hybridized with a STRITC (here on referred to as PO-$SiO_2$-STRITC). Substrates were heated at T=155° C., which induces retraction of the substrate and causes the $SiO_2$ thin film to buckle and crack.

Figure 17:
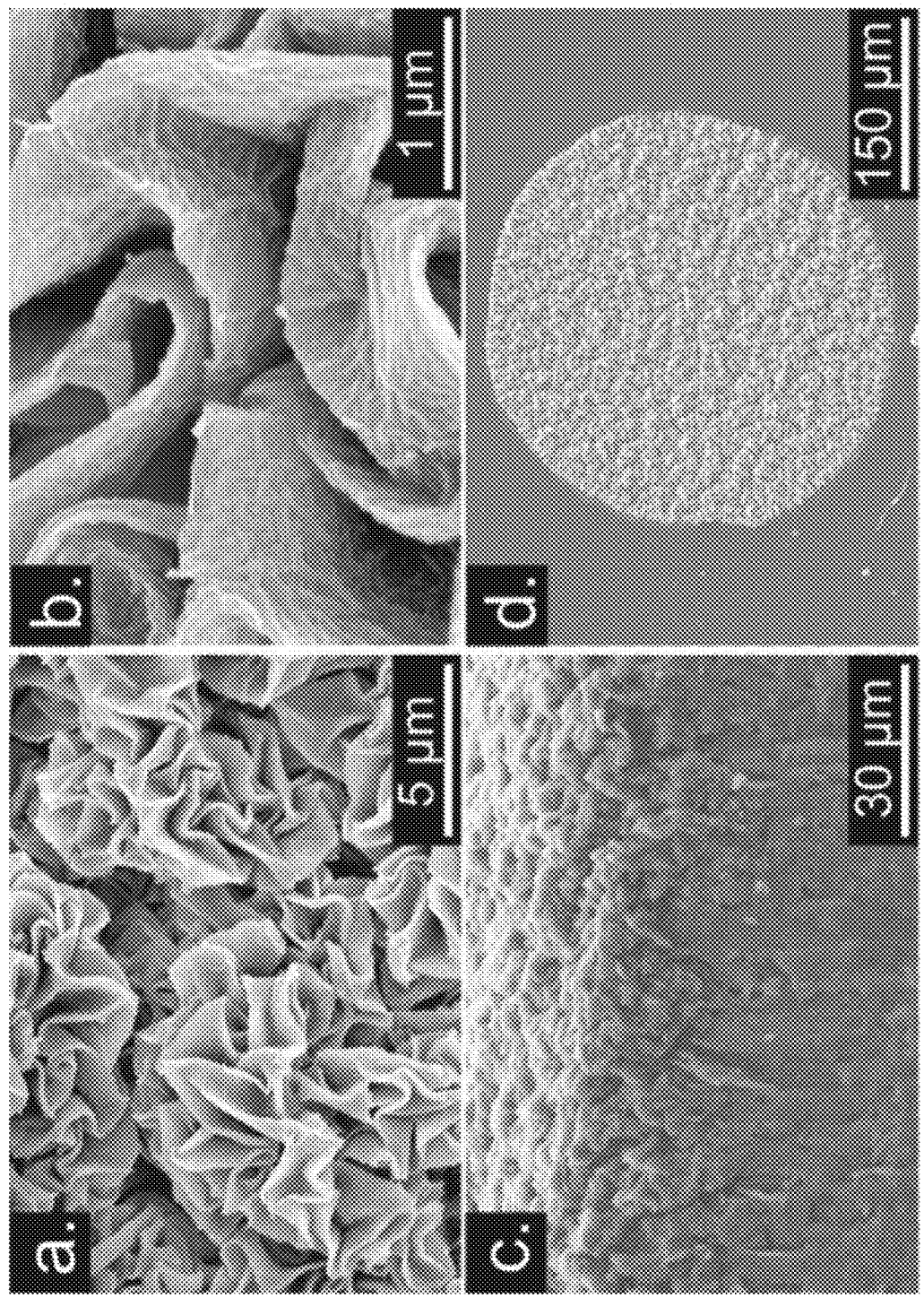
FIG. 17. SEM images of the PO-SiO$_2$ substrate. Top down SEM images of shrunk PO-SiO2 substrate showing micro- and nanostructures at different magnifications (a) and (b) and a cross section SEM image of the PO-SiO$_2$ substrate (c). The PO film can be patterned to form discrete SiO$_2$ islands (d).

FIGS. 17(*a*) and (*b*) are top down SEM images of the shrunk PO-$SiO_2$ substrate. The SEM image illustrates the formation of a continuous population of heterogeneous surface structures. The cross section SEM image (FIG. 17*c*) demonstrates integration of the $SiO_2$ layer with the PO film that occurs when the PO film is heated above its glass transition temperature. Integration of the $SiO_2$ into the PO film is also supported from energy dispersive X-ray spectroscopy (EDS) data. The $SiO_2$ structures are patterned into distinct islands by applying a shadow mask prior to $SiO_2$ deposition (FIG. 17*d*).

Optical Characterization

Figure 18:
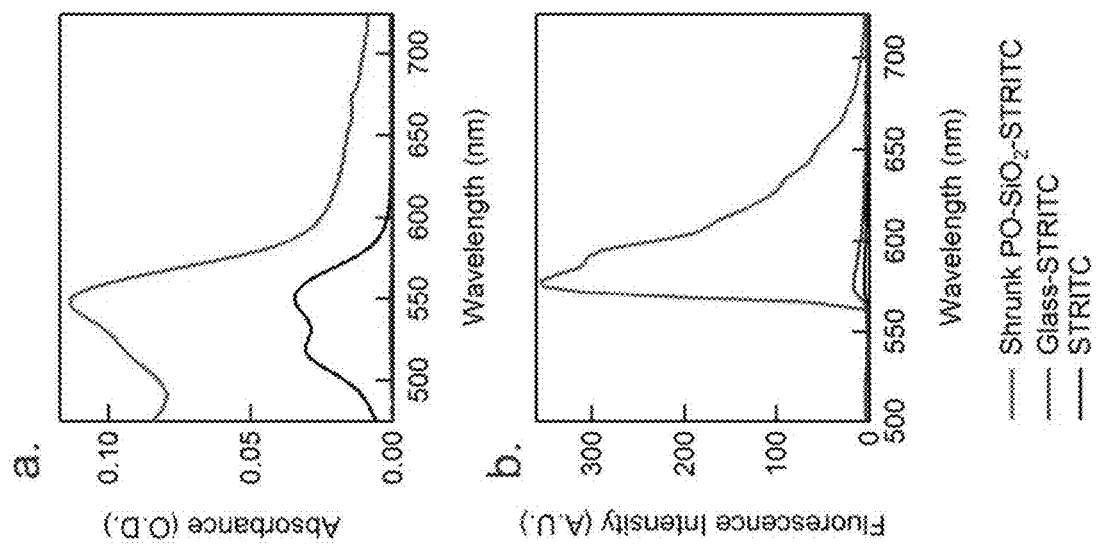
FIG. 18. Absorption spectra of STRITC free dye, glass-STRITC, and PO-SiO$_2$-STRITC (a). Emission spectra of STRITC free dye, glass-STRITC, and PO-SiO$_2$-STRITC (b).

To examine the effects of the $SiO_2$ structures on the photophysical properties of the linked fluorescent dye, optical properties of the reacted substrate and controls were measured. The UV-Vis absorption spectra of STRITC, glass-STRITC (STRITC bound to glass), and shrunk PO-$SiO_2$-STRITC are shown in FIG. 18*a*. STRITC exhibits two absorption maxima at 520 and 549 nm attributed to the presence of dimeric and monomeric species reported to occur for rhodamine dyes at high concentrations (A 520/549=0.89) (F. del Monte et al. 2000 *Langmuir* 16: 7377-7382). Glass-STRITC also exhibits an absorption maximum at 549 nm. Covalent linkage of STRITC within the $SiO_2$ structures is not observed to cause spectral shifts in peak absorbance. The absorption spectra of the shrunk PO-$SiO_2$-STRITC substrate shows higher optical density at higher energies, which fits well to Rayleigh scattering, suggesting that shrinking of the PO-$SiO_2$ substrate creates rough porous structures with small surface features that together result in light scattering (J. Dakin and R. G. W. Brown, in *Handbook of Optoelectronics*, Taylor & Francis, New York 2006; and A. T. Young 1981 Appl. Optics 20: 533-535).

The emission spectra are shown in FIG. 18*b*. The emission intensity maximum for the STRITC occurs at 575 nm. While covalent attachment of the STRITC on glass does not cause a change in the absorption wavelength, it is observed to cause a slight red shift of 3.0 nm for the emission wavelength for STRITC on the PO-$SiO_2$ substrate. This slight red shift in emission wavelength can be attributed to the change in molecular surrounding experienced by the STRITC dye since it is known that dye molecules are affected by microenvironment polarity (J. R. Lakowicz in *Principles of Fluorescence Spectroscopy*, 3rd ed., Springer, New York 2006). However, the observed spectral shifts are insignificant and it can be suggested that confinement of the dye molecules within the $SiO_2$ structures does not result in changes of the dye's electronic structure.

Fluorescence Signal Enhancement on PO-$SiO_2$ Substrate

Figure 8:
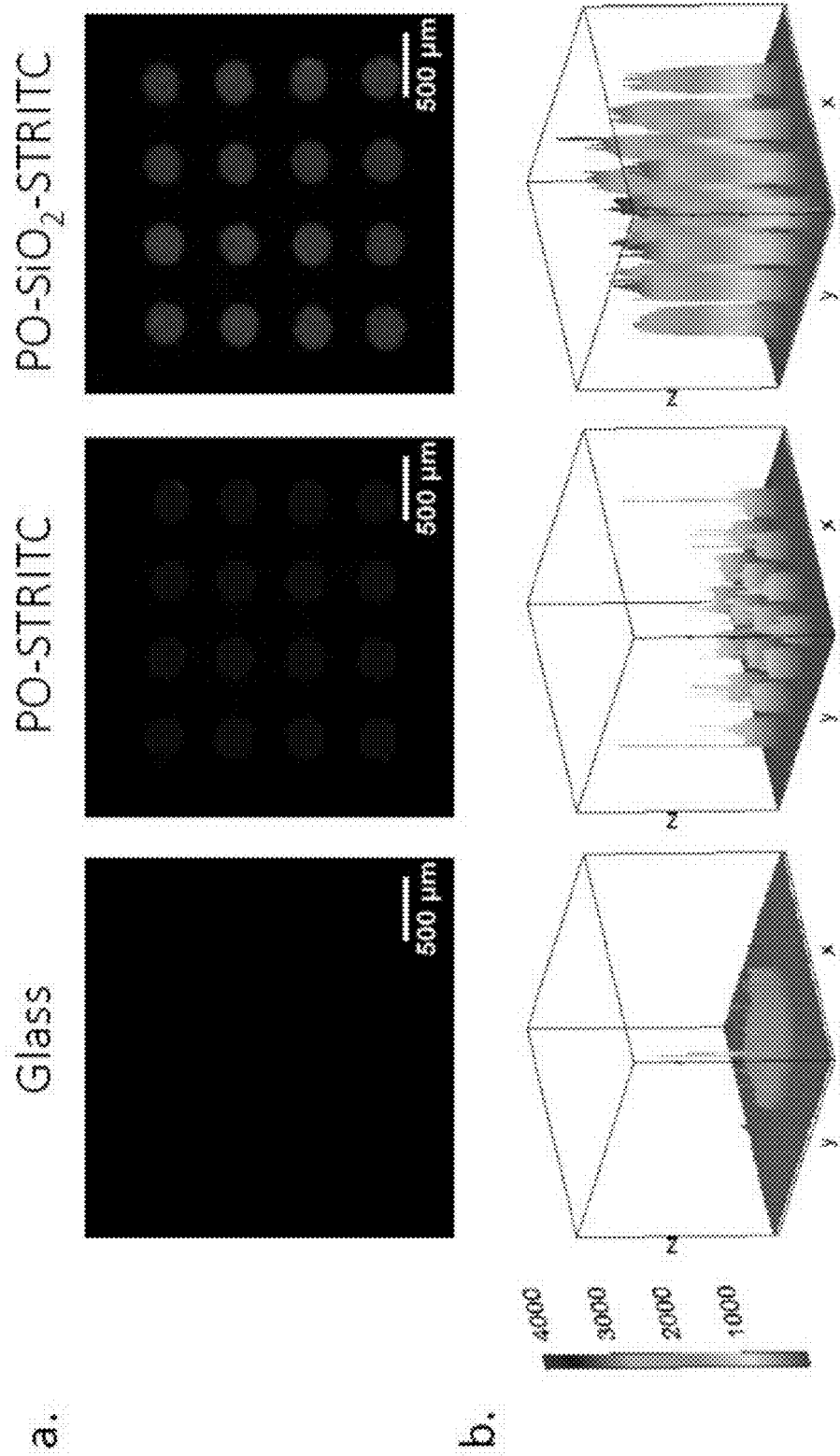
FIG. 8.(a) shows fluorescent images of the patterned substrates of heated glass, thermally shrunk PO, and thermally shrunk PO-SiO$_2$ bound with biotin and TRITC-conjugated streptavidin; (b) shows the corresponding 3D fluorescence intensity profiles.

Fluorescence signal enhancement on PO-$SiO_2$ substrates were investigated using the model biotin-streptavidin binding system. Substrates were prepared as described above and shrunk thermally. The fluorescence images of the patterned substrates following shrinkage are shown in FIG. 8*a*. The 3D intensity distribution profiles (FIG. 8*b*) illustrate fluorescence uniformity over the $SiO_2$ islands on the shrunk PO-$SiO_2$-STRITC substrates and that enhanced fluorescence signal is not localized to nanometric hotspots. The increase in fluorescence signal is assessed and results are compared to that obtained on glass-STRITC and thermally shrunk PO (PO-STRITC). The average fluorescence signal increase (SI) of the substrate is calculated to be the fluorescence signal obtained after shrinking minus the background (here defined as the substrate without the presence of dye), over the fluorescence signal before shrinking minus the background:

$$SI = \frac{Intensity_{postshrunk} - Intensity_{postshrunk,bg}}{Intensity_{preshrunk} - Intensity_{preshrunk,bg}} \quad (1)$$

As previously reported, the PO film experiences a 77% reduction in each length upon heating, which results in a theoretical 20-fold consolidation of surface area (D. Nguyen et al. 2010 *Lab Chip* 10: 1623-1626). The PO-STRITC experiences a fluorescence SI of 14-fold (standard error (SE)=0.57) due to concentration of the surface bound fluorophores. This slight decrease in experimental value compared to the theoretical expectation is attributed to concentration quenching effect from bringing the fluorescent molecules close in proximity. Interestingly, an approximate 50-fold (SE=1.9) fluorescence SI is observed on the shrunk PO-SiO$_2$-STRITC substrates. Notably, the fluorescence SI is accompanied with a significantly increased SNR (defined as the ratio of the raw fluorescence signal to the background signal) from 11:1 to 76:1. The increased fluorescence intensity from shrinking the PO-SiO$_2$-STRITC substrate exceeds that observed from just concentrating the fluorescent molecules (as seen on the PO-STRITC substrate). This suggests that the additional increase of fluorescence signal on the PO-SiO$_2$-STRITC substrate is due to presence of SiO$_2$ structures and not from bringing the fluorophores into close proximity of each other. We also show on the glass surface that the application of heat does not cause signal amplification or significant signal degradation (SI, glass=0.92, SE=0.019) and that the SNR does not change considerably (from 5.7:1 to 5.2:1 following heating). Therefore the observed increase in fluorescence intensity on the shrunk PO-STRITC and the shrunk PO-SiO$_2$-STRITC cannot be attributed to changes in the fluorophore due to heating. For comparison between substrates, the average fluorescence enhancement factors (EFs) are calculated. The fluorescence EF is defined to be the fluorescence intensity of substrate minus the background over the fluorescence intensity of the comparison substrate minus its respective background:

$$EF = \frac{Intensity_{exp,postshrunk} - Intensity_{exp,bg}}{Intensity_{control,postshrunk} - Intensity_{control,bg}} \quad (2)$$

Compared to the glass-STRITC, the shrunk PO-SiO$_2$-STRITC substrate has an average fluorescence EF of 116 (SE=9.7). We observe a higher fluorescence signal on the flat PO-SiO$_2$-STRITC relative to glass-STRITC, and we attribute the higher signal to the increased surface area that forms during the sputter deposition of SiO$_2$. Increased surface area subsequently allows for an increased number of binding sites for biomolecule attachment. To distinguish between concentrating surface biomolecules and additional effects from the SiO$_2$ structures, the EF of the shrunk PO-SiO$_2$-STRITC substrate over the shrunk PO-STRITC is evaluated. Experimental results suggest that the SiO$_2$ structures contributes in an additional 5.0-fold enhancement (SE=0.74) of fluorescence signal on top of the concentrating effects.

Binding Study with Alternate Dye

While fluorescence enhancements that arise from plasmon resonances are highly dependent on nanostructure size and shape (S. Link and M. A. El-Sayed 2000 *Int. Rev. Phys. Chem.* 19: 409-453), we show that increased fluorescence signal and fluorescence enhancement factors on our PO-SiO$_2$ substrates are not restricted to a particular wavelength or structure size. 10 µg mL$^{-1}$ Cy2-conjugated streptavidin were spotted onto unshrunk biotinylated substrates as previously performed. Upon shrinking the substrate, a 39-fold (SE=1.6) and 11-fold (SE=1.2) increase in the fluorescence signal is observed on the shrunk PO-SiO$_2$ substrate and the shrunk PO substrate, respectively. The increases in fluorescence signal correspond to averaged enhancement factors of 106 (SE=9.5) and 5.0 (SE=0.27) for the shrunk PO-SiO$_2$ relative to the heated glass and shrunk PO substrate. An increase in SNR is also experienced on the shrunk PO-SiO$_2$ substrate from 13:1 to 29:1.

Lower Limits of Detection

Figure 9:
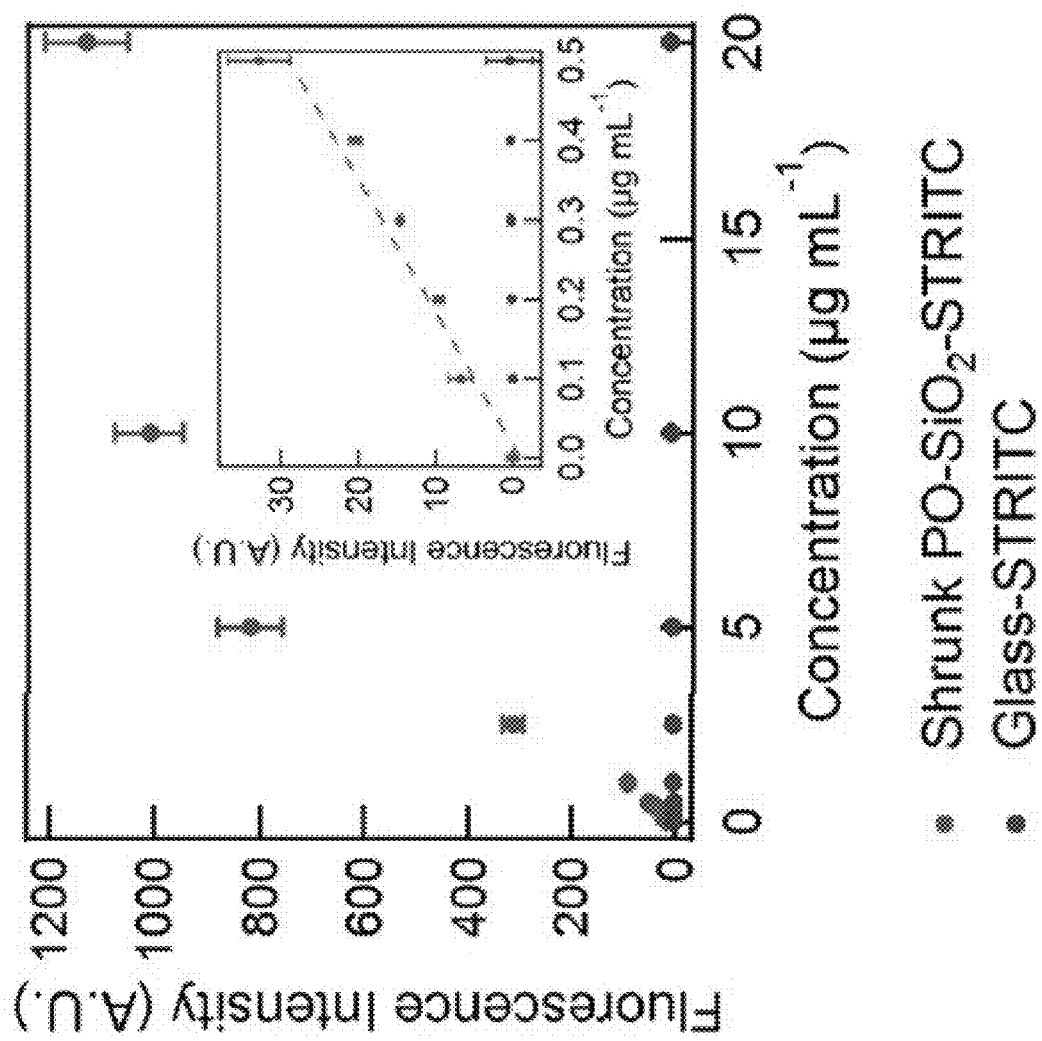
FIG. 9. A graph demonstrating lowered limits of detection (LOD) on the PO-SiO$_2$ substrates.
Figure 10:
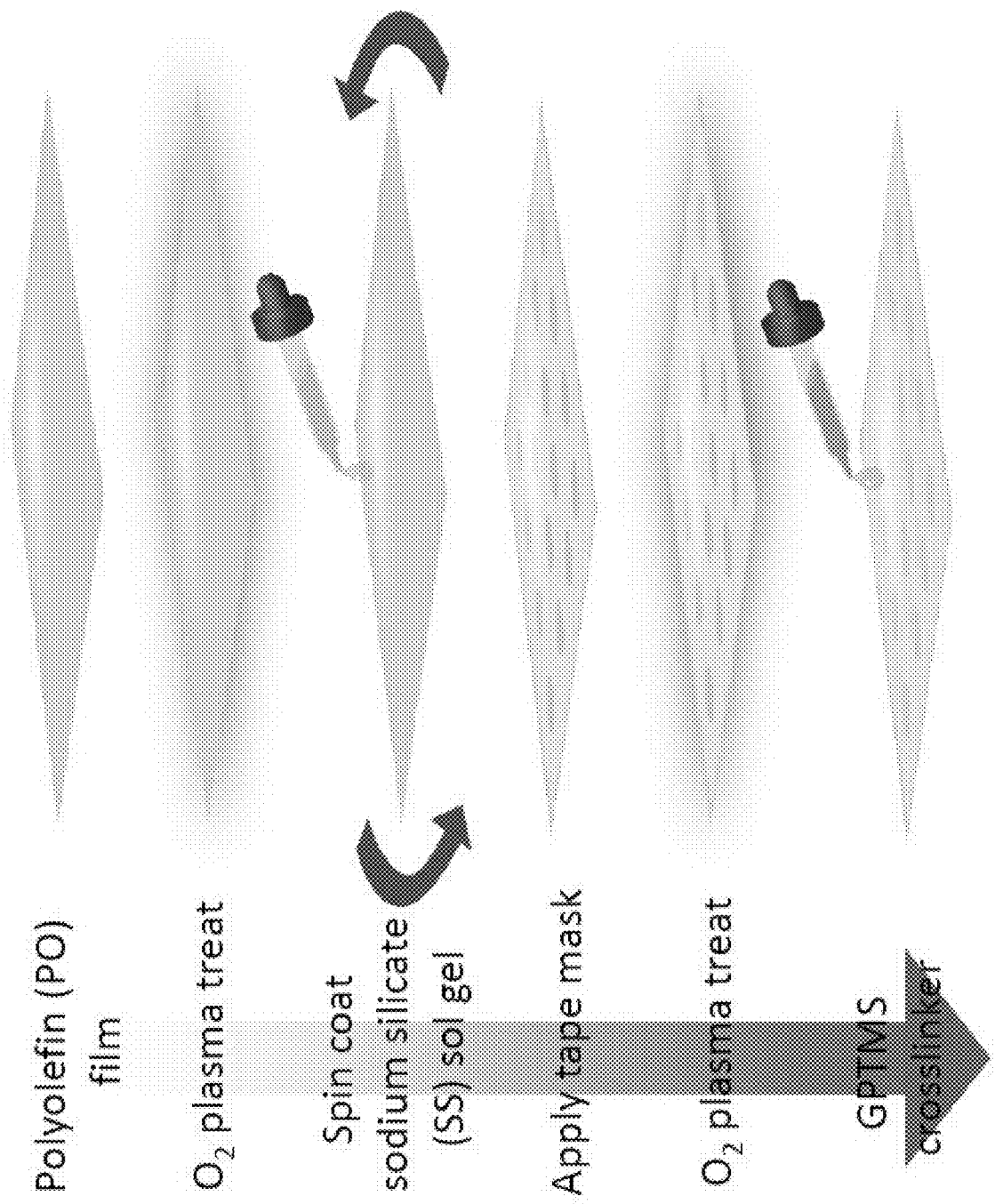
FIG. 10. A schematic illustration outlining an example substrate fabrication process. The resulting sol-gel coated PO film is sometimes referred to herein as PO-SS.
Figure 11:
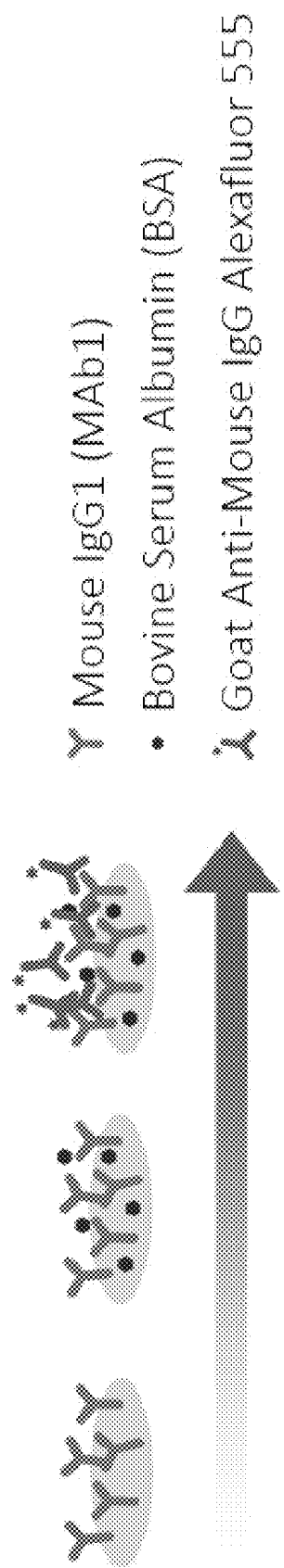
FIG. 11. A schematic illustration outlining an example immunoassay performed on functionalized PO-SS prior to shrinkage. Shrinkage of the PO-SS substrate following the immunoassay results in signal increase.
Figure 12:
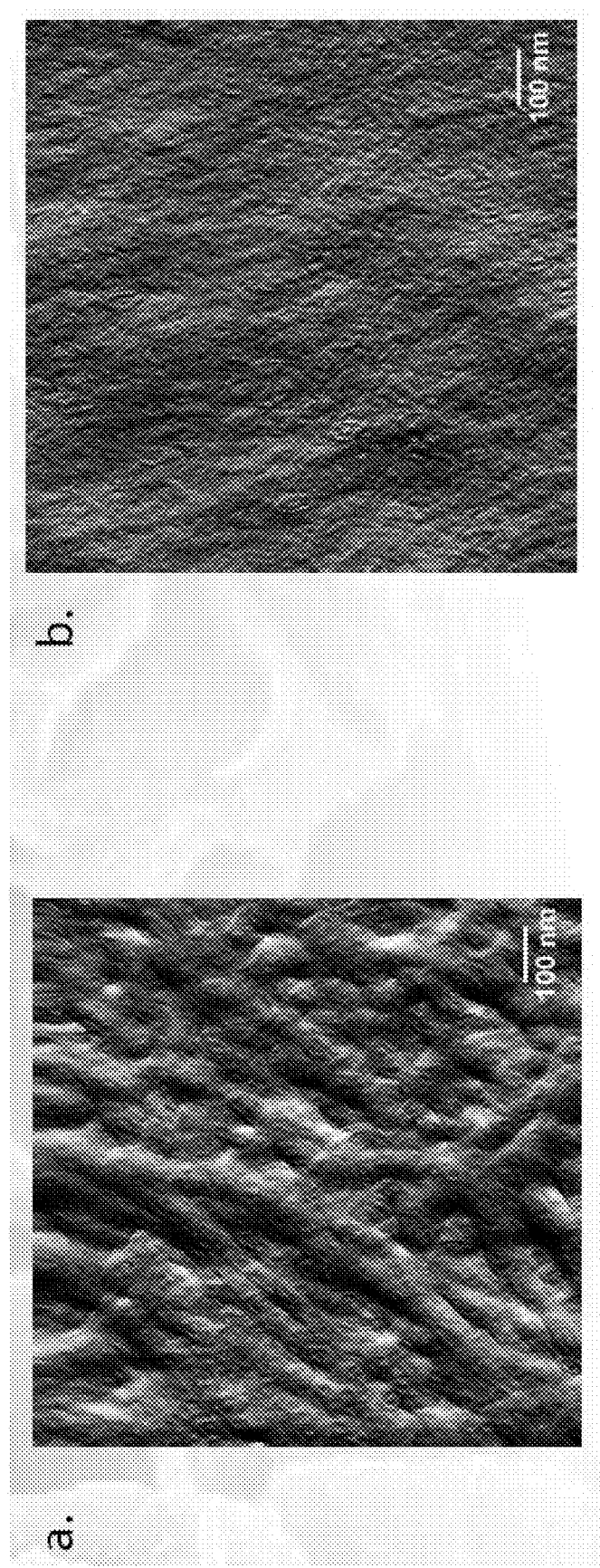
FIG. 12.(a) and (b) are atomic force microscopy (AFM) characterization of the PO film before and after sol-gel deposition, respectively.
Figure 13:
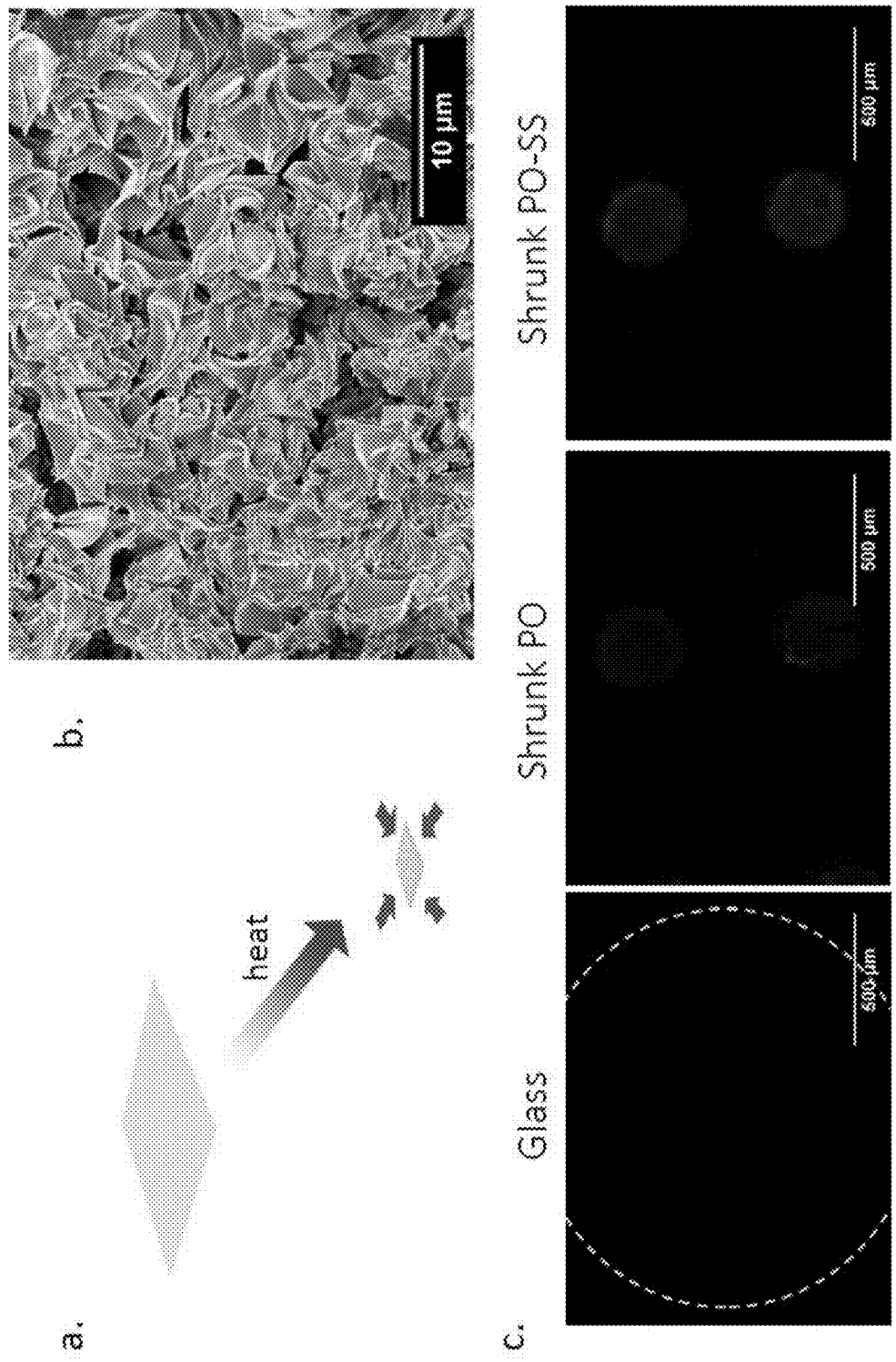
FIG. 13. (a) is a schematic of PO-SS substrate undergoing shrinking process. (b) is a SEM image of the resulting silica structures. (c) shows fluorescence intensity images of immunoassay on different substrates shows that there is an increased signal on shrink PO-SS.
Figure 14:
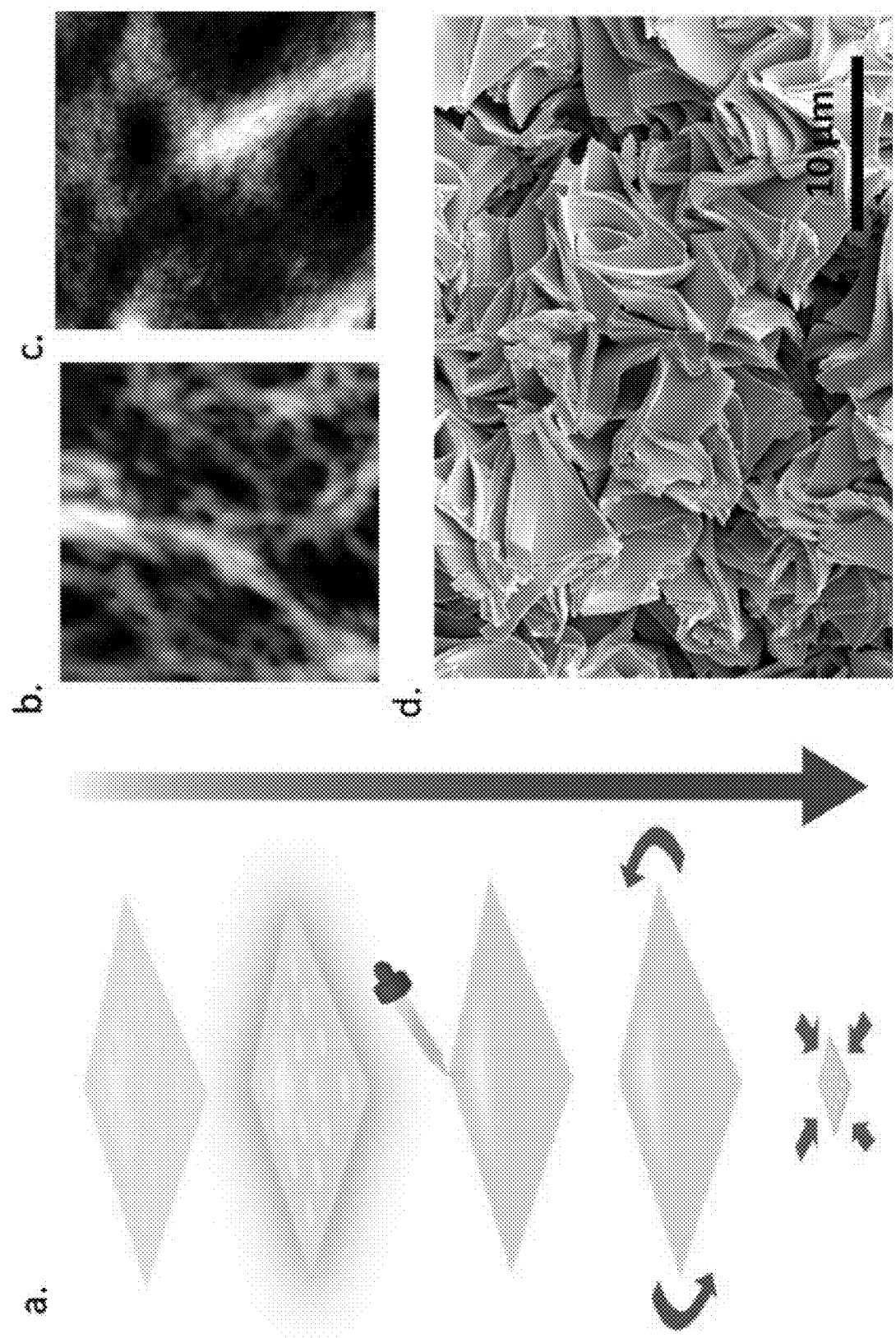
FIG. 14. Selective patterning of silica onto treated surfaces. (a) First, regions desired for silica deposition are defined using a shadow mask. The mask is applied on a clean surface. The entire surface is then plasma treated to introduce surface hydroxyl groups. The shadow mask is removed and a sol-gel solution is then spin coated onto the surface, adhering only to the regions that were exposed to the plasma. AFM data shows a change in surface topography following spin coating of the silica sol-gel; (b) represents uncoated; (c) represents coated. Upon shrinkage of the thermoplastic polymer, regions of the exposed silica islands are shown (d).

To evaluate detection sensitivity of the PO-SiO$_2$ substrates, a concentration curve of STRITC was performed on the PO-SiO$_2$ and glass substrate. We use the biotin-streptavidin hybridization since this system can be applied towards real immunoassays through DNA, protein, or aptamer linking. The results are plotted in FIG. 9. The fluorescence signal corresponding to the limit of detection (LOD) is defined to be the mean of the background plus three times the standard deviation of the background. The LOD is calculated to be 0.26 µg mL$^{-1}$ (SE=0.026) on the heated glass surface. In contrast, the shrunk PO-SiO$_2$ substrate is able to yield a lower LOD of 11 ng mL$^{-1}$ (SE=0.0027). This proof-of-concept demonstrates that the PO-SiO$_2$ substrate has higher detection sensitivity relative to planar glass surface. This ability to reach lower limits of detection suggests the possibility for applications in disease diagnostics and point-of-care testing.

Conclusion

In this work, we have presented a rapid method to create SiO$_2$ micro- and nanostructures, demonstrated the ability of our structures to enhance fluorescence signal of bound fluorophores, and achieved lower limits of detection on the PO-SiO$_2$ substrates. We also investigated the photophysical properties of the dye on the SiO$_2$ structures. Fabrication of SiO$_2$ structures is simple and rapid, leading to signal enhancement within minutes. Structures are directly integrated on chip and defined regions of SiO$_2$ structures are easily established. The observed far-field fluorescence enhancements on our structures are robust and highly reproducible.

Due to the well-established conjugation chemistries and high biocompatibility of SiO$_2$, our PO-SiO$_2$ substrate has applications in surface sensing technologies. Integration of our SiO$_2$ structures into microfluidic devices for point-of-care applications is readily realized as similar structures have been demonstrated to be robustly integrated into the plastic used for microfluidic chips (D. Nawarathna et al. 2012 *Appl. Phys. Lett.* 102).

Experimental Section

Fabrication of Functionalized PO-SiO$_2$ Substrate: PO film (955-D, Sealed Air Corporation) was cleaned in isopropyl alcohol (IPA) and double deionized water (ddH$_2$O) and dried with pressurized air. To pattern discrete regions of SiO$_2$, a sealing tape mask (Nunc) was applied to the clean PO film surface prior to SiO$_2$ deposition. A mask composed of a four-by-four array of circles with radii of 7.0 µm was designed using automated Computer-Aided-Design (AutoCAD) software and cut with a VersaLASER cutter. Following application of the sealing tape mask, the PO surface was then coated with SiO$_2$ using an ion-beam sputter coater at deposition time of 20 min (MODEL IBS/e, South Bay Technology, Inc.). The SiO$_2$-modified PO substrates (PO-SiO$_2$) were treated with oxygen plasma (Plasma Prep II, SPI supplies) for 5 min and then immersed into a solution of 3-(aminopropyl)trimethoxysilane (APTMS) in ethanol (2% v/v) for 45 min at room temperature. The samples were rinsed with ethanol and ddH$_2$O, dried with pressurized air, and cured overnight in ambient conditions. Amine-functionalized PO-SiO$_2$ substrates were used immediately after preparation.

Binding Study: A model immunoassay was performed by reacting silanized PO-SiO$_2$ surfaces with EZ-Link Sulfo-NHS-LC-biotin (0.10 mg mL$^{-1}$) (Piercenet Thermoscientific) for 1 h at room temperature. The surfaces were washed, dried with pressurized air, and spotted with tetramethylrhodamine isothiocyanate (TRITC)-conjugated streptavidin (10 µg mL$^{-1}$) (Jackson ImmunoResearch Inc.). Substrates were incubated in a humidified chamber for 1 h before washing and drying, and shrunk by applying heat at 155° C. for 3 min. Fluorescent images were taken using a custom built upright fluorescence microscope (Olympus) using a 2× objective (NA=0.055, Edmond Optics) and analyzed using ImageJ.

Characterization of SiO$_2$ Substrates: Shrunk PO-SiO$_2$ surface structures were characterized using scanning electron microscopy (SEM). Shrunk PO-SiO$_2$ substrates were sputter coated with 7.0 nm gold (Q150R S, Quorum Technologies) and SEM images were obtained with 10 kV beam and 12 mm working distance (Hitachi S-4700-2 FE-SEM Scanning Electron Microscope). Energy-dispersive X-ray spectroscopy (EDS) of substrate composition was performed on shrunk PO-SiO$_2$ sputtered with 7.0 nm gold and obtained with a 10 kV beam and 12 mm working distance (Philips XL-30 FEG Scanning Electron Microscope).

Optical Properties: UV-visible absorption spectra were collected using a PerkinElmer Lambda 950 UV/Vis/NIR Spectrophotometer with the help of the Law group. For highly scattering surfaces, a 60 mm integrating sphere was used. Fluorescence spectra were measured with an excitation wavelength of 561 nm and emission was collected from 416-728 nm (Zeiss LSM 710) using a 20× objective (NA=0.4, Zeiss Korr C-Apochromat) and an argon laser.

Lower Limits of Detection: PO-SiO$_2$ and glass substrates were biotinylated as previously described. Surfaces were spotted with stock concentrations of STRITC (20, 10, 5, 2.5, 1.0, 0.50, 0.40, 0.30, 0.20, 0.10, and 0.0 µg mL$^{-1}$) and incubated per conditions described above. Following heating at T=155° C., samples were imaged as previously described.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method of detecting a biological agent deposited on a surface of a polyolefin polymer film comprising:
    applying a shadow mask to the polyolefin polymer film to define blocked regions and exposed regions of the polyolefin polymer film;
    functionalizing the surface of the polyolefin polymer film with oxygen plasma treatment to introduce hydroxyl groups at the exposed regions but not at the blocked regions of the polyolefin polymer film;
    removing the shadow mask from the polyolefin polymer film following functionalization of the surface;
    coating the functionalized polyolefin polymer film with a sol-gel solution containing the biological agent and silica precursors suspended or dissolved in a liquid;
    activating the silica precursors by adding an acid or a base to the sol-gel solution, wherein the activated silica precursors react with the hydroxyl groups of the polyolefin polymer film and with each other to form a solid SiO$_2$ network encapsulating the biological agent, wherein the solid SiO$_2$ network is deposited as solid SiO$_2$ encapsulating the biological agent onto the surface of the polyolefin polymer film only to the regions that were exposed to the functionalizing treatment;
    heat-shrinking the polyolefin polymer film; and
    detecting the biological agent.

2. The method of claim 1, wherein the biological agent is an analyte, a protein or a nucleic acid.

3. A method of detecting a biological agent deposited on a surface of a polyolefin polymer film comprising:
    applying a shadow mask to the polyolefin polymer film to define blocked regions and exposed regions of the polyolefin polymer film;

functionalizing the surface of the polyolefin polymer film with oxygen plasma treatment to introduce hydroxyl groups at the exposed regions but not at the blocked regions of the polyolefin polymer film;

removing the shadow mask from the polyolefin polymer film following functionalization of the surface;

coating the functionalized polyolefin polymer film with a sol-gel solution containing silica precursors suspended or dissolved in a liquid; and activating the silica precursors by adding an acid or a base to the sol-gel solution, wherein the activated silica precursors react with the hydroxyl groups of the polyolefin polymer film and with each other to form a solid $SiO_2$ network, wherein the solid $SiO_2$ network is deposited as solid $SiO_2$ onto the surface of the polyolefin polymer film only to the regions that were exposed to the functionalizing treatment;

binding a biological agent to silica already deposited onto the surface of the polyolefin polymer film;

heat-shrinking the polyolefin polymer film; and detecting the biological agent.

4. The method of claim 3, wherein the biological agent is an analyte, a protein or a nucleic acid.

5. A method of making an immunoassay platform comprising a silica-encapsulated first detection agent deposited on a polyolefin polymer substrate, the method comprising:

using a shadow mask to define blocked regions and exposed regions of the polyolefin polymer substrate;

functionalizing a surface of the polyolefin polymer substrate with oxygen plasma treatment to introduce hydroxyl groups at the exposed regions but not at the blocked regions of the polyolefin polymer substrate;

removing the shadow mask from the polyolefin polymer substrate following functionalization of the surface;

coating the functionalized polyolefin polymer substrate with a sol-gel solution containing silica precursors and the first detecting agent;

activating the silica precursors by adding an acid or a base to the sol-gel solution, wherein the activated silica precursors react with the hydroxyl groups of the polyolefin polymer substrate and with each other to form a solid $SiO_2$ network, wherein solid $SiO_2$, encapsulating the first detecting agent, is deposited onto the surface of the polyolefin polymer substrate only to the regions that were exposed to the functionalizing treatment; and heat-shrinking the polyolefin polymer substrate.

* * * * *